United States Patent
Jacob et al.

(10) Patent No.: US 10,513,736 B2
(45) Date of Patent: *Dec. 24, 2019

(54) MIRNA BIOMARKERS FOR MONITORING BONE MARROW RECONSTITUTION

(71) Applicant: OHIO STATE INNOVATION FOUNDATION, Columbus, OH (US)

(72) Inventors: Naduparambil Jacob, Dublin, OH (US); Arnab Chakravarti, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/195,411

(22) Filed: Nov. 19, 2018

(65) Prior Publication Data

US 2019/0177795 A1    Jun. 13, 2019

Related U.S. Application Data

(63) Continuation of application No. 15/310,594, filed as application No. PCT/US2015/030888 on May 14, 2015, now Pat. No. 10,131,952.

(60) Provisional application No. 61/996,669, filed on May 14, 2014.

(51) Int. Cl.
   *C12Q 1/6883* (2018.01)
   *A61K 31/56* (2006.01)

(52) U.S. Cl.
   CPC ............ *C12Q 1/6883* (2013.01); *A61K 31/56* (2013.01); *C12Q 2600/178* (2013.01)

(58) Field of Classification Search
   CPC . C12Q 1/6883; C12Q 2600/178; A61K 31/56
   USPC ....................................................... 514/110
   See application file for complete search history.

(56) References Cited

U.S. PATENT DOCUMENTS 10,131,952 B2 * 11/2018 Jacob .................. C12Q 1/6883
2014/0024700 A1    1/2014 Van Rooij et al.
2014/0341841 A1   11/2014 Jacob et al.

FOREIGN PATENT DOCUMENTS

WO       2011127219 A1    10/2011

OTHER PUBLICATIONS

Jacob, et al., "Identification of Sensitive Serum microRNA Biomarkers for Radiation Biodosimetry", PLoS One (2013) 8:2, e57603.
Brunck, et al., "Concise Review: Next-Generation Cell Therapies to Prevent Infections in Neuropenic Patients", StemCellTM (2014), 541-548.
International Search Report and Written Opinion issued in International Application No. PCT/US2015/030888, dated Oct. 16, 2015.
International Preliminary Report on Patentability issued in International Application No. PCT/US2015/030888, dated Nov. 24, 2016.
Szyper-Kravitz, et al., "Granulocyte colony-stimulating factor administration upregulates telomerase activity in CD34 haemopoietic cells and may prevent telomere attrition after chemotherapy", British J Haematology (2003), 120, 329-336.
Urdea, "Branched DNA Signal Amplification", Nature Biotechnology (1994), 12:926-928.
Bartel DP, "MicroRNAs: genomics, biogenesis, mechanism, and function", Cell (2004) 116: 281-297.
Iorio MV, et al. "MicroRNA dysregulation in cancer: diagnostics, monitoring and therapeutics. A comprehensive review", EMBO Mol Med (2012) 4:143-159.
Cui W, et al. "Plasma miRNA as Biomarkers for Assessment of TotalBody Radiation Exposure Dosimetry", PLoS One (2011) 6: e22988.
Scholl V, et al., "miRNA-451: A putative predictor marker of Imatinib therapy response in chronic myeloid leukemia", Leuk. Res (2012) 36:119-121.
Qi P, et al. "Serum MicroRNAs as Biomarkers for Hepatocellular Carcinoma in Chinese Patients with Chronic Hepatitis B Virus Infection",PLoS One (2011) 6: e28486.
Weiland M, et al. "Small RNAs have a large impact",RNA Biol (2012) 9: 850-859.
Cortez MA, et al. "MicroRNAs in body fluids—the mix of hormones and biomarkers",Nat Rev Clin Oncol (2011) 8: 467-477.
Russo F, et al. "miRandola: Extracellular Circulating MicroRNAs Database", PLoS One (2012) 7: e47786.
Hunter MP, et al., "Detection of microRNA Expression in Human Peripheral Blood Microvesicles", PLoS One (2008) 3:e3694.
Valadi H, et al. "Exosome-mediated transfer of mRNAs and microRNAs is a novel mechanism of genetic exchange between cells",Nat Cell Biol (2007) 9: 654-659.

(Continued)

*Primary Examiner* — Kristin A Vajda
(74) *Attorney, Agent, or Firm* — Meunier Carlin & Curfman LLC

(57) ABSTRACT

Disclosed herein are compositions and methods for monitoring hematopoietic reconstitution or suppression in a subject. Also disclosed are compositions and methods for reconstituting the hematopoietic compartment of a subject in need thereof. Also disclosed is a method for monitoring the effect of ionizing radiation on the lung in a subject. Also disclosed is the ability to use detection of the one or more microRNA indicative of radiation-induced lung injury to guide therapy of the subject. Also disclosed is the ability to use detection of the one or more microRNA indicative of radiation-induced lung injury to evaluate the efficacy of a lung treatment following radiation exposure.

27 Claims, 31 Drawing Sheets

(56) References Cited

OTHER PUBLICATIONS

Etheridge A, et al., "Extracellular microRNA: a new source of biomarkers", Mutat Res (2011) 717: 85-90.
Geiss GK, et al. "Direct multiplexed measurement of gene expression with color-coded probe pairs", Nat Biotechnol (2008) 26: 317-325.
Wang B, et al. "Stat3-mediated activation of miR-23a suppresses gluconeogenesis in hepatocellular carcinoma by downregulating G6PC and PGC-1α", Hepatology (2012) 56: 186-197.
Thum T, et al. "MicroRNA-21 contributes to myocardial disease by stimulating MAP kinase signalling in fibroblasts",Nature (2008) 456: 980-984.
Teichler S, et al. "MicroRNA29a regulates the expression of the nuclear oncogene Ski", Blood (2011) 118:1899-1902.
Vasilescu C, et al., "MicroRNA Fingerprints Identify miR-150 as a Plasma Prognostic Marker in Patients with Sepsis", PLoS One (2009) 4: e7405.
Zhou B, et al. "miR-150, a microRNA expressed in mature B and T cells, blocks early B cell development when expressed prematurely",Proc Natl Acad Sci U S A (2007)104: 7080-7085.
Waselenko JK, et al. "Medical Management of the Acute Radiation Syndrome: Recommendations of the Strategic National Stockpile Radiation Working Group", Ann Intern Med (2004) 140:1037-1051.
Blakely WF, et al. "Biodosimetry medical recording-use of the Biodosimetry Assessment Tool", (2010) Health Phys 99 Suppl 5: S184-191.
Gowns RE, et al. "Early dose assessment following severe radiation accidents" Health Phys (1997) 72: 513-518, abstract.
Prasanna, P.G., et al. (2010) "Synopsis of partial-body radiation diagnostic biomarkers and medical management of radiation injury workshop.", Radiat Res 173(2):245-53.
Rea, M.E., et al. "Proposed triage categories for large-scale radiation incidents using high-accuracy biodosimetry methods", (2010) Health Phys 98(2):136-44.
Dicarlo, A.L., et al. "Radiation Injury After a Nuclear Detonation: Medical Consequences and the Need for Scarce Resources Allocation", (2011) Disaster Med Public Health Prep 5 Suppl 1:S32-44.
Garofalo, M., et al. "The delayed pulmonary syndrome following acute high-dose irradiation: a rhesus macaque model", (2014) Health Phys 106(1):56-72.

Mitchell, P.S., et al. "Circulating microRNAs as stable blood-based markers for cancer detection",Proc Natl Acad Sci U S A (2008) 105(30):10513-8.
Templin, T., et al., "Whole mouse blood microRNA as biomarkers for exposure to γ-rays and 56Fe ions" Int J Radiat Biol. (2012) 87(7):653-62.
Barcellos-Hoff, M.H., et al., "How do tissues respond to damage at the cellular level? The role of cytokines in irradiated tissues", (1998) Radiat Res 150(5 Suppl):S109-20.
Zhu, Y., et al. "MicroRNA-21 is involved in ionizing radiation-promoted liver carcinogenesis", Int J Clin Exp Med (2010) 3(3):211-22.
Davis, B.N., et al., "SMAD proteins control DROSHA-mediated microRNA maturation", (2008) Nature 454(7200):56-61.
Zhang, X., et al., "The ATM kinase induces microRNA biogenesis in the DNA damage response", (2011) Mol Cell 41(4):371-83.
Garzon, R., et al. "MicroRNAs in normal and malignant hematopoiesis", (2008) Curr Opin Hematol 15(4):352-8, abstract.
Adams, B.D., et al., "An In Vivo Functional Screen Uncovers miR-150-Mediated Regulation of Hematopoietic Injury Response", (2012) Cell Rep 2(4):1048-60.
Xiao, C., et al. "MiR-150 Controls B Cell Differentiation by Targeting the Transcription Factor c-Myb",Cell (2007) 131(1):146-59.
Jiang, X., et al. "Blockade of miR-150 maturation by MLL-fusion/MYC/LIN-28 is required for MLL-associated leukemia", Cancer Cell (2012) 22(4):524-35.
Bezman, N.A., et al., "miR-150 regulates the development of NK and iNKT cells", J Exp Med (2011) 208(13):2717-31.
Rube, C.E., et al., "Dose-dependent induction of transforming growth factor beta (TGF-beta) in the lung tissue of fibrosis-prone mice after thoracic irradiation", Int J Radiat Oncol Biol Phys (2000), 47(4):1033-42.
Hassan, F., et al., "MiR-101 and miR-144 Regulate the Expression of the CFTR Chloride Channel in the Lung", PLoS One (2012) 7(11):e50837.
Izzotti, A., et al., "Downregulation of microRNA expression in the lungs of rats exposed to cigarette smoke", (2009) Faseb J 23(3):806-12.
Oglesby, I.K., et al. "miR-126 is downregulated in cystic fibrosis airway epithelial cells and regulates TOM1 expression", (2010) J Immunol 184(4):1702-9.

* cited by examiner

CBA/J

| FL. COUNT IN 20 μl | % | microRNA |
|---|---|---|
| 6895 | 23.10 | miR-451 |
| 3776 | 12.65 | miR-16 |
| 1179 | 3.95 | miR-21 |
| 969 | 3.25 | miR-23a |
| 923 | 3.09 | miR-22 |
| 846 | 2.83 | miR-150 |
| 678 | 2.27 | miR-25 |
| 633 | 2.12 | miR-546 |
| 553 | 1.85 | miR-223 |
| 479 | 1.60 | miR-145 |
| 388 | 1.30 | miR-720 |
| 351 | 1.18 | miR-30b |
| 334 | 1.12 | miR-29a |
| 316 | 1.06 | miR-106a+17 |
| 310 | 1.04 | miR-27a |
| 281 | 0.94 | miR-30d |
| 253 | 0.85 | let-7g |
| 248 | 0.83 | miR-205 |
| 248 | 0.83 | miR-125b-5p |
| 239 | 0.80 | miR-24 |
| 220 | 0.74 | miR-106b |
| 206 | 0.69 | miR-1902 |
| 192 | 0.64 | miR-762 |
| 191 | 0.64 | miR-130a |
| 185 | 0.62 | miR-30a |
| 180 | 0.60 | miR-20a+20b |
| 176 | 0.59 | miR-19a |
| 174 | 0.58 | miR-126-3p |
| 169 | 0.57 | miR-191 |
| 160 | 0.54 | miR-146a |
| 157 | 0.53 | miR-148a |
| 155 | 0.52 | let-7c |
| 149 | 0.50 | miR-144 |
| 146 | 0.49 | miR-574-3p |
| 131 | 0.44 | miR-203 |
| 127 | 0.42 | miR-93 |
| 120 | 0.40 | miR-122 |
| 109 | 0.36 | miR-486 |
| 106 | 0.35 | miR-126-5p |
| 104 | 0.35 | miR-29c |
| 101 | 0.34 | miR-1937a+1937b |
| 98 | 0.33 | miR-30e |
| 96 | 0.32 | miR-199a-3p |
| 93 | 0.31 | miR-2137 |
| 87 | 0.29 | let-7b |
| 86 | 0.29 | miR-19b |
| 80 | 0.27 | miR-378 |
| 79 | 0.27 | miR-222 |
| 75 | 0.25 | miR-2183 |
| 75 | 0.25 | miR-883a-3p |

| FL. COUNT IN 20 μl | % | microRNA |
|---|---|---|
| 8423 | 22.03 | miR-451 |
| 4718 | 12.34 | miR-16 |
| 1704 | 4.46 | miR-22 |
| 1575 | 4.12 | miR-150 |
| 1385 | 3.62 | miR-25 |
| 1359 | 3.55 | miR-21 |
| 1230 | 3.22 | miR-223 |
| 1186 | 3.10 | miR-23a |
| 1102 | 2.88 | miR-29a |
| 623 | 1.63 | miR-486 |
| 590 | 1.54 | miR-125b-5p |
| 482 | 1.26 | let-7g |
| 440 | 1.15 | miR-130a |
| 421 | 1.10 | miR-106a+17 |
| 401 | 1.05 | miR-30b |
| 386 | 1.01 | miR-191 |
| 330 | 0.86 | miR-30d |
| 326 | 0.85 | let-7c |
| 315 | 0.82 | miR-2137 |
| 307 | 0.80 | miR-126-3p |
| 299 | 0.78 | miR-720 |
| 289 | 0.76 | miR-27a |
| 271 | 0.71 | miR-145 |
| 215 | 0.56 | miR-148a |
| 209 | 0.55 | miR-19a |
| 204 | 0.53 | miR-328 |
| 204 | 0.53 | miR-146a |
| 202 | 0.53 | let-7b |
| 200 | 0.52 | miR-378 |
| 197 | 0.51 | miR-20a+20b |
| 185 | 0.48 | miR-30a |
| 176 | 0.46 | miR-24 |
| 173 | 0.45 | miR-762 |
| 157 | 0.41 | miR-122 |
| 155 | 0.40 | miR-1902 |
| 143 | 0.37 | miR-106b |
| 135 | 0.35 | miR-29c |
| 133 | 0.35 | miR-342-3p |
| 123 | 0.32 | miR-199a-3p |
| 122 | 0.32 | miR-205 |
| 114 | 0.30 | miR-93 |
| 110 | 0.29 | miR-574-3p |
| 100 | 0.26 | miR-125a-5p |
| 100 | 0.26 | miR-19b |
| 98 | 0.26 | miR-2133 |
| 97 | 0.25 | miR-350 |
| 91 | 0.24 | miR-140 |
| 91 | 0.24 | miR-126-5p |
| 91 | 0.24 | miR-669f |
| 89 | 0.23 | miR-709 |

*FIGURE 2B*

|  | Control | 1 Gy | 2 Gy | 4 Gy | 6 Gy | 8 Gy |
|---|---|---|---|---|---|---|
| 24 hrs | 100% | 70% | 62% | 52% | 30% | 28% |
| 48 hrs | 100% | 50% | 35% | 20% | 14% | 12% |

FRACTIONATION SCHEDULE 24 h: 2 x 2 = 4 Gy;   SERUM: DAY 2

48 h: 4 x 2 = 8 Gy;   SERUM: DAY 3

72 h: 6 x 2 = 12 Gy;   SERUM: DAY 4

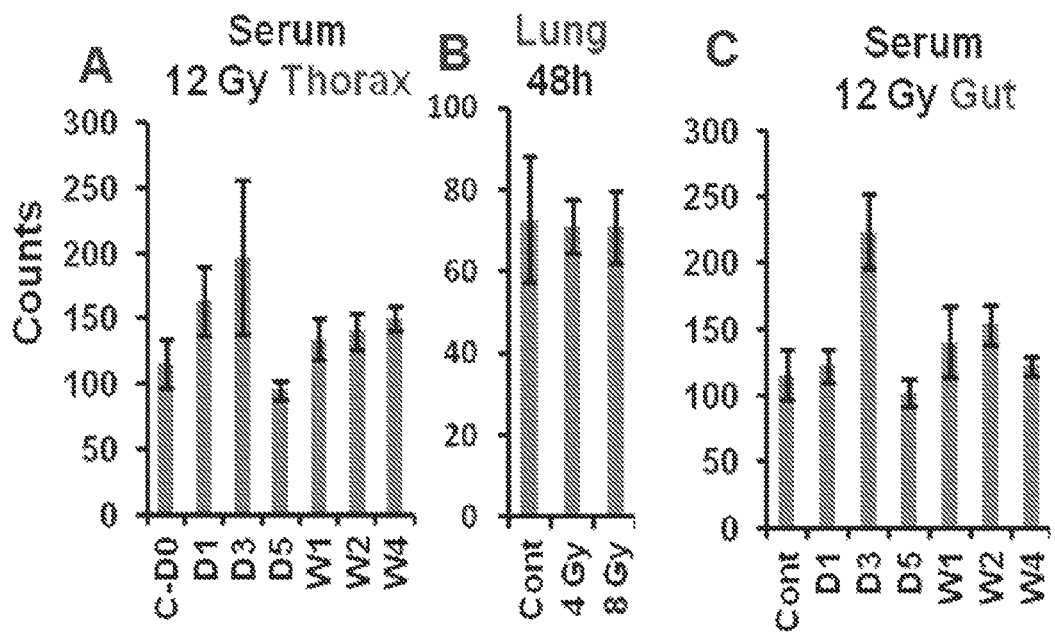
*Figures 11A to 11C*
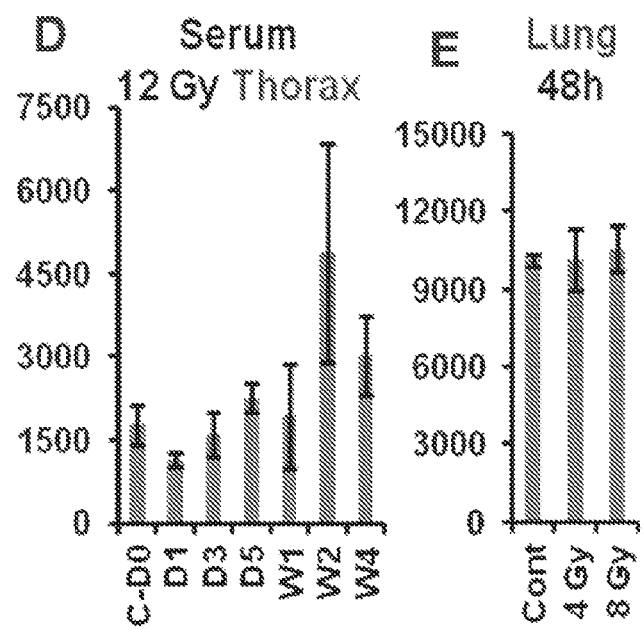
*Figure 11D*  *Figure 11E*

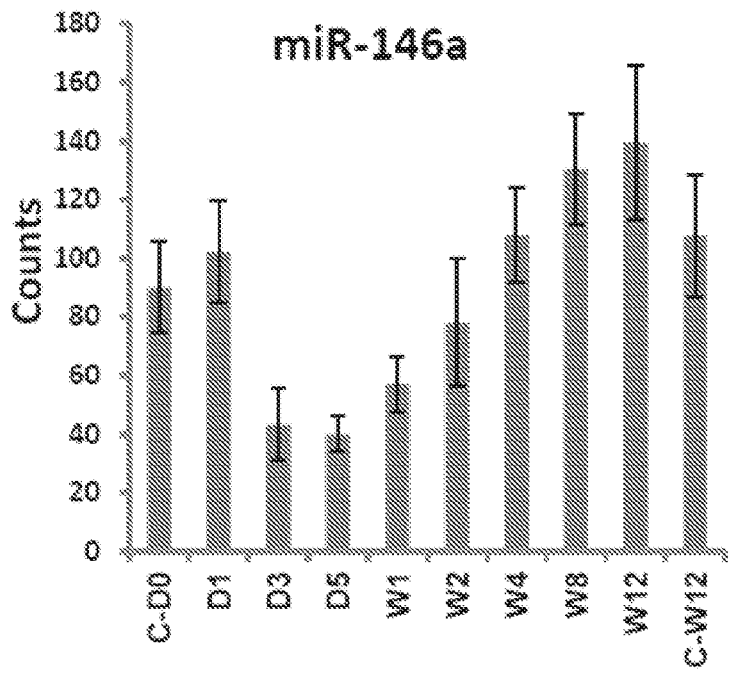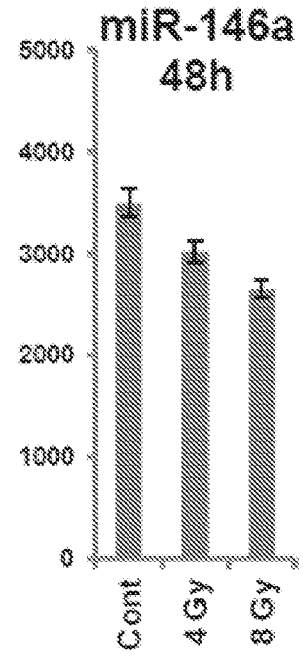
*Figure 15I*          *Figure 15J*
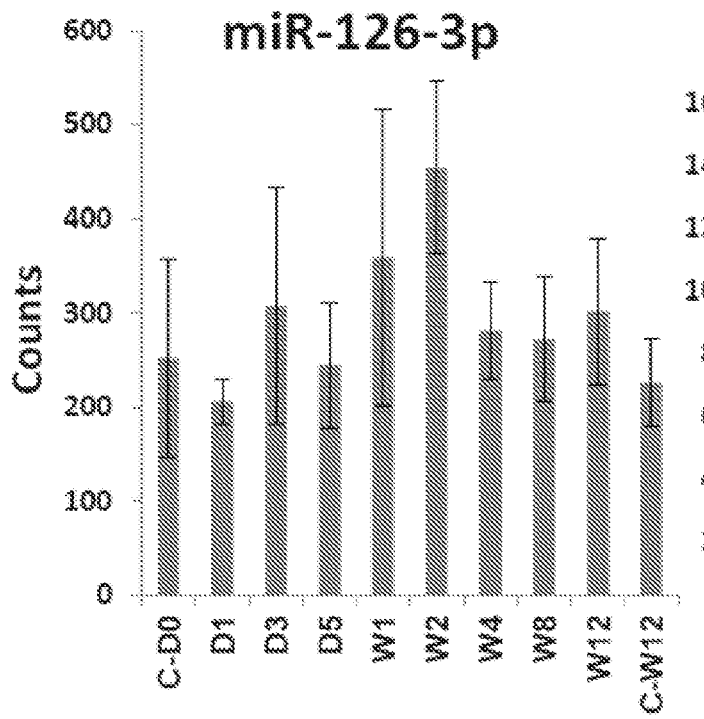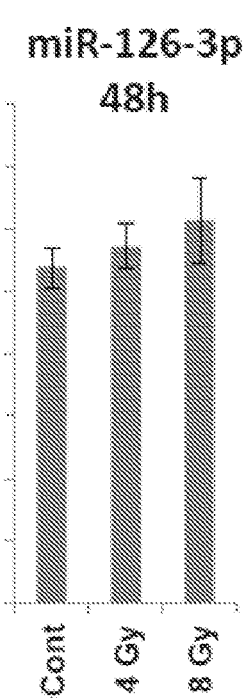
*Figure 15K*          *Figure 15L* microCT -Lung

WTLI- Pneu

Control

MIRNA BIOMARKERS FOR MONITORING BONE MARROW RECONSTITUTION

CROSS-REFERENCE TO RELATED APPLICATIONS

This application claims benefit of U.S. Provisional Application No. 61/996,669, filed May 14, 2014, the disclosure of which is hereby incorporated herein by reference in its entirety.

BACKGROUND

The use of hematopoietic stem cells for bone marrow transplantation has revolutionized the approaches used to treat a large number of hematological malignancies, autoimmune diseases, and immunodeficiencies. The use of hematopoietic stem cell transplantations has also been successful in mitigating the effects of exposure to high levels of radiation. In addition, hematopoietic stem cell transplantations have been used to enable administration of high doses of cytotoxic chemotherapeutic agents to patients who suffer from a number of solid organ tumors, thus enabling the repopulation of the bone marrow following drug-induced toxicity. The use of hematopoietic stem cell transplantation to improve the rate of engraftment of solid organ transplantations is another recent application of this medical procedure. Recent studies also indicate that bone marrow transplantation may have value in the treatment of heart disease. These therapeutic applications of hematopoietic stem cell transplantation demonstrate the medical and economic impact of improving hematopoietic stem cell transplantation, including methods for monitoring the efficacy of bone marrow reconstitution.

Radiation-induced lung disease (RILD) is a frequent complication of radiotherapy to the chest for chest wall or intrathoracic malignancies and can have a variety of appearances, especially depending on when the patient is imaged. Acute and late phases are described, corresponding to radiation pneumonitis and radiation fibrosis respectively. These occur at different times after completion of radiotherapy and have different imaging features and differential diagnoses. Methods for early detection of RILD would allow reduction in dosage and/or early treatment to minimizing damage to the lung.

SUMMARY

Disclosed herein are compositions and methods for monitoring hematopoietic constitution (e.g., reconstitution or suppression) in a subject. The methods can therefore also be used to diagnose the status of the bone marrow, e.g., following a radiation or cytotoxic exposure. The methods generally involve quantifying the levels of circulating miR-150 in a cell-free blood sample from the subject, wherein the levels of circulating miR-150 in the sample is a measure of hematopoietic reconstitution or suppression. For example, in some cases, the subject is the recipient of a hematopoietic stem cell transplantation (e.g., following myeloablation).

The method can further involve determining in the sample the levels of at least one internal control miRNA whose blood levels are not dependent on bone marrow constitution. These internal control miRNA levels can then be used to normalize the miR-150 levels. Examples of miRNAs whose levels are not sensitive to bone marrow constitution and therefore can be used as internal controls include miR-30a, miR-23a, miR130b, and miR-302d-3p.

Also disclosed are compositions and methods for reconstituting the hematopoietic compartment of a subject in need thereof. The methods can involve administering to the subject a therapeutically effective amount of a population of hematopoietic stem cells to reconstitute the hematopoietic compartment of the subject; and then monitoring (e.g., serially) the efficacy of the hematopoietic reconstitution by quantifying the levels of circulating miR-150 in a cell-free blood sample from the subject. In these embodiments, the levels of circulating miR-150 in the sample can be an indication of hematopoietic reconstitution.

In some embodiments, the disclosed radiation-sensitive miRNAs are present in blood cells. Therefore, contamination of miRNA from blood cells, e.g., by hemolysis, can mask circulating miRNAs that are bone marrow specific. Therefore, in some embodiments, the disclosed method can further involve determining in the sample the levels of at least one hemolysis control miRNA whose presence in the sample is an indication of hemolysis contamination. In these embodiments, hemolysis contamination can be an indication that the sample should be discarded. Examples of miRNAs whose levels are an indication of hemolysis contamination include miR-451, miR-16, miR-25, miR-106b, let-7g, and miR-93.

To control for variances in the starting material as well as the efficiency of RNA extraction steps used for miRNA measurements, known amounts of spike-in controls can be used to control for these variations. The disclosed method can therefore also involve spiking the sample with known amounts of at least one oligonucleotide, and determining in the sample levels of the at least one oligonucleotide to further normalize the radiation-sensitive miRNA levels. Examples of suitable oligonucleotides include synthetic microRNAs.

In some embodiments, the subject has or had a hematological malignancy, myeloma, multiple myeloma, acute myeloid leukemia (AML), leukemia, acute lymphoblastic leukemia, chronic lymphocytic leukemia, a lymphoma, indolent lymphoma, non-Hodgkin lymphoma, diffuse B cell lymphoma, follicular lymphoma, mantle cell lymphoma, T cell lymphoma, Hodgkin lymphoma, a neuroblastoma, a retinoblastoma, Shwachman Diamond syndrome, a brain tumor, Ewing's Sarcoma, a Desmoplastic small round cell tumor, a relapsed germ cell tumor, a hematological disorder, a hemoglobinopathy, an autoimmune disorder, juvenile idiopathic arthritis, systemic lupus erythematosus, severe combined immunodeficiency, congenital neutropenia with defective stem cells, severe aplastic anemia, a sickle-cell disease, a myelodysplasia syndrome, chronic granulomatous disease, a metabolic disorder, Hurler syndrome, Gaucher disease, osteopetrosis, malignant infantile osteopetrosis, heart disease, HIV, or AIDS. In some cases, the subject has had an organ transplant.

The population of hematopoietic stem cells can be obtained from many suitable sources, including, for example, bone marrow, peripheral blood cells, peripheral blood cells that have undergone apheresis, peripheral blood cells that have undergone leukapheresis, umbilical cord blood, amniotic fluid, cultured HSC cells, an immortalized HSC cell line, or a conditionally immortalized HSC cell line.

In some embodiments, the population of hematopoietic stem cells is administered as a step in a hematopoietic stem cell (HSC) transplantation procedure. For example, the HSC transplantation procedure can be a myeloablative HSC transplantation procedure or a non-myeloablative HSC transplantation procedure. In some cases, the HSC transplantation can be an autologous HSC transplantation or an allogenic HSC transplantation.

Also disclosed is a method for monitoring the effect of ionizing radiation on the lung in a subject. The method can involve quantifying the levels of one or more circulating microRNA in a cell-free blood sample from the subject, elevated levels of which are an indication of radiation-induced lung injury.

In some embodiments, the microRNA are selected from the group consisting of let-7c, miR-15b, miR-21, miR-25, miR-29a, miR-126-3p, miR-142-3p, miR-144-3p, miR-146a, miR-191-5p, miR-192, miR-200b, and miR-486. For example, in some cases, elevated levels of miR-200b, miR-191-5p, miR-144-3p, miR-146a, miR-142-3p, miR-192, or a combination thereof, occurring in the first week after exposure is an indication of lung tissue damage. In some cases, elevated levels of miR-21, miR-29a, miR-126-3p, let-7c, miR-191-5p, miR-15b, or a combination thereof, occurring about two to four weeks after exposure is an indication of lung inflammatory response and injury. In some cases, elevated levels of miR-146a, miR-486, miR-25, miR-192, or a combination thereof, occurring about eight weeks after exposure is an indication of pneumonitis.

The method can further involve determining in the sample the levels of at least one internal control miRNA whose blood levels are not dependent on bone marrow constitution. These internal control miRNA levels can then be used to normalize the one or more microRNA indicative of radiation-induced lung injury levels. Examples of miRNAs whose levels are not sensitive to bone marrow constitution and therefore can be used as internal controls include miR-30a, miR-23a, miR130b, and miR-302d-3p.

Also disclosed is the ability to use detection of the one or more microRNA indicative of radiation-induced lung injury can be used to guide therapy of the subject. In some embodiments, the method involves treating the subject for lung injury if elevated levels of the one or more circulating microRNA are detected. For example, the method can involve treating the subject with a corticosteroid, angiotensin converting enzyme inhibitors (ACEI), hydroxymethylglutaryl coenzyme A (HMG-CoA) reductase inhibitor, cyclophosphamide, N-acetylcysteine (NAC), supplemental oxygen therapy, or a combination thereof if elevated levels of the one or more circulating microRNA are detected. In some embodiments, the method involves reducing the radiation dose if elevated levels of the one or more circulating microRNA are detected.

Also disclosed is the ability to use detection of the one or more microRNA indicative of radiation-induced lung injury to evaluate the efficacy of a lung treatment following radiation exposure. For example, this can involve monitoring levels of the one or more circulating microRNA in a cell-free blood sample from the subject taken at intervals following the treatment and wherein a reduction in levels of the one or more microRNA is an indication that the treatment is effective.

The details of one or more embodiments of the invention are set forth in the accompa-nying drawings and the description below. Other features, objects, and advantages of the invention will be apparent from the description and drawings, and from the claims.

DESCRIPTION OF DRAWINGS

FIGS. 2A and 2B are lists of miRNAs detected in 20 µl serum from mice strains CBA/J (FIG. 2A) and C57BL/6 (FIG. 2B), arranged in their order of abundance (%) based on average signal (counts) detected.

FIG. 5A shows the dose dependent depletion of serum miRNA-150 at 24 hrs (p-values: 1 Gy-0.0164, 2 Gy-0.0191, 4 Gy-0.0026, 6 Gy-0.0001, 8 Gy-0.0001). FIG. 5B shows counts from a non-responsive molecule miRNA-23a, comparable to that of miRNA-150 in control animals. FIGS. 5C and 5D show radiation induced increase in miRNA-200b and miRNA-762 (p-values, miRNA-200b:1 Gy-0.7172, 2 Gy-0.4193, 4 Gy-0.4231, 6 Gy-0.0421, 8 Gy-0.0296; miRNA-762:1 Gy-0.4061, 2 Gy-0.1675, 4 Gy-0.0324, 6 Gy-0.3139, 8 Gy-0.001).

FIG. 8A shows the dose dependent depletion of serum miRNA-150 at different time points during and after fractionation (p-values: 4 Gy-0.0003, 8 Gy-0.0001, 12 Gy-0.0001). FIG. 8B shows counts from a non-responsive molecule miRNA-23a (control). FIGS. 8C and 8D shows radiation induced increases in miRNA-200b (p-values 4 Gy-0.014, 8 Gy-0.0047, 12 Gy 0.0027) and miRNA-762.

FIGS. 11A to 11E show kinetics of serum miR-192 (FIGS. 11A to 11C) and miR-21 (FIGS. 11D and 11E) after WTLI (12 Gy) and Gut IR (12 Gy). Multiplex nCounter® assay was used to compare miRNAs in serum separated from blood collected on Day 1, 3, 5, Week 1, 2, and 4 after irradiation (n=6). Samples from age matched unirradiated animals were used as control. Counts (expression level) of the miRNAs in lung tissue also are shown.

DETAILED DESCRIPTION

Figure 1A:
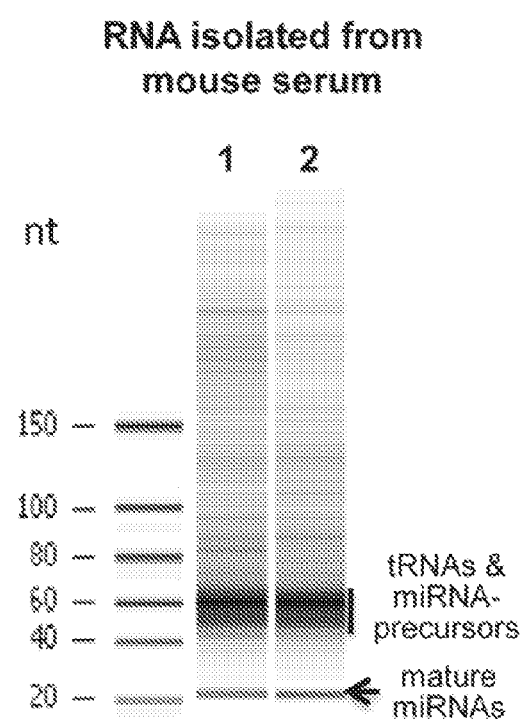
FIG. 1A is a gel image showing the integrity of RNA isolated from two mouse serum samples.

Disclosed are miRNA biomarkers that may be used to monitor hematopoietic constitution (e.g., reconstitution or suppression) in the bone marrow of a subject, as well as miRNA biomarkers that may be used to monitor the effect of ionizing radiation on the lung in a subject. In some embodiments, the methods entail detection of extracellular, circulating miRNAs in a suitable sample, preferably blood, plasma, serum, urine, or saliva.

In some embodiments, the biological sample used for determining the level of one or more miRNA biomarkers is a sample containing circulating miRNAs, e.g., extracellular miRNAs. Circulating miRNAs include miRNAs in cells (cellular miRNA), extracellular miRNAs in microvesicles (microvesicle-associated miRNA), and extracellular miRNAs that are not associated with cells or microvesicles (extracellular, non-vesicular miRNA).

Extracellular miRNAs freely circulate in a wide range of bodily fluids. Accordingly, in some embodiments, the biological sample used for determining the level of one or more miRNA biomarkers is a bodily fluid, such as blood, fractions thereof, serum, plasma, urine, saliva, tears, sweat, semen, vaginal secretions, lymph, bronchial secretions, or CSF. In some embodiments, the sample is a sample that is obtained non-invasively. In some embodiments, the sample is obtained from a bodily fluid other than CSF. In some embodiments, the biological sample used for determining the level of one or more miRNA biomarkers may contain cells. In other embodiments, the biological sample may be free or substantially free of cells (e.g., a serum or plasma sample). The sample may likewise be free or substantially free of microvesicles. For example, a sample that is free or substantially free of microvesicles is one in which the microvesicle content of the sample is sufficiently low to avoid interfering with the ability to accurately determine the level of non-vesicular miRNAs in the sample.

The level of one or more miRNA biomarkers in a biological sample may be determined by any suitable method. Any reliable method for measuring the level or amount of miRNA in a sample may be used. Generally, miRNA can be detected and quantified from a sample (including fractions thereof), such as samples of isolated RNA by various methods known for mRNA detection, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString™ analysis, Northern Blot analysis, branched DNA (bDNA) signal amplification, and in situ hybridization), and sequencing-based methods (e.g. next-generation sequencing methods, for example, using the Illumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the mirVana TaqMan® miRNA transcription kit (Ambion, Austin, Tex.), and the TaqMan® miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In other embodiments, the level of miRNA is measured during the amplification process. In still other embodiments, the level of miRNA is not amplified prior to measurement. Some exemplary methods suitable for determining the level of miRNA in a sample are described in greater detail below. These methods are provided by way of illustration only, and it will be apparent to a skilled person that other suitable methods may likewise be used.

Many amplification-based methods exist for detecting the level of miRNA nucleic acid sequences, including, but not limited to, PCR, RT-PCR, qPCR, and rolling circle amplification. Other amplification-based techniques include, for example, ligase chain reaction, multiplex ligatable probe amplification, in vitro transcription (IVT), strand displacement amplification, transcription-mediated amplification, RNA (Eberwine) amplification, and other methods that are known to persons skilled in the art.

A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer. Kits for quantitative real time PCR of miRNA are known, and are commercially available. Examples of suitable kits include, but are not limited to, the TaqMan® miRNA Assay (Applied Biosystems) and the mirVana™ qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence.

In some instances, custom qRT-PCR assays can be developed for determination of miRNA levels. Custom qRT-PCR assays to measure miRNAs in a biological sample, e.g., a body fluid, can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in biological samples.

Amplification curves may optionally be checked to verify that Ct values are assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the 2(-ΔΔ C(T)) Method.

In some embodiments, two or more miRNAs are amplified in a single reaction volume. For example, multiplex q-PCR, such as qRT-PCR, enables simultaneous amplification and quantification of at least two miRNAs of interest in one reaction volume by using more than one pair of primers and/or more than one probe. The primer pairs comprise at least one amplification primer that specifically binds each miRNA, and the probes are labeled such that they are distinguishable from one another, thus allowing simultaneous quantification of multiple miRNAs.

Rolling circle amplification is a DNA-polymerase driven reaction that can replicate circularized oligonucleotide probes with either linear or geometric kinetics under isothermal conditions. In the presence of two primers, one hybridizing to the (+) strand of DNA, and the other hybridizing to the (−) strand, a complex pattern of strand displacement results in the generation of over $10^9$ copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations.

miRNA may also be detected using hybridization-based methods, including but not limited to hybridization arrays (e.g., microarrays), NanoString™ analysis, Northern Blot analysis, branched DNA (bDNA) signal amplification, and in situ hybridization.

Microarrays can be used to measure the expression levels of large numbers of miRNAs simultaneously. Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays. Also useful are microfluidic TaqMan Low-Density Arrays, which are based on an array of microfluidic qRT-PCR reactions, as well as related microfluidic qRT-PCR based methods.

In one example of microarray detection, various oligonucleotides (e.g., 200+5'-amino-modified-C6 oligos) corresponding to human sense miRNA sequences are spotted on three-dimensional CodeLink slides (GE Health/Amersham Biosciences) at a final concentration of about 20 μM and processed according to manufacturer's recommendations. First strand cDNA synthesized from 20 μg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol.

Axon B-4000 scanner and Gene-Pix Pro 4.0 software or other suitable software can be used to scan images. Non-positive spots after background subtraction, and outliers detected by the ESD procedure, are removed. The resulting signal intensity values may be normalized to per-chip median values and then used to obtain geometric means and standard errors for each miRNA. Each miRNA signal can be transformed to log base 2, and a one-sample t test can be conducted. Independent hybridizations for each sample can be performed on chips with each miRNA spotted multiple times to increase the robustness of the data.

Microarrays can be used for the expression profiling of miRNAs in diseases. For example, RNA can be extracted from a sample and, optionally, the miRNAs are size-selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the, capture probes are affixed. The spot will then fluoresce when excited using a microarray laser scanner.

The fluorescence intensity of each spot is then evaluated in terms of the number of copies of a particular miRNA, using a number of positive and negative controls and array data normalization methods, which will result in assessment of the level of expression of a particular miRNA.

Total RNA containing the miRNA extracted from a body fluid sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA.

Several types of microarrays can be employed including, but not limited to, spotted oligonucleotide microarrays, pre-fabricated oligonucleotide microarrays or spotted long oligonucleotide arrays.

miRNAs can also be detected without amplification using the nCounter®) Analysis System (NanoString™ Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter® miRNA assay kits are available from NanoString™ Technologies, which are capable of distinguishing between highly similar miRNAs with great specificity.

miRNAs can also be detected using branched DNA (bDNA) signal amplification (see, for example, Urdea, Nature Biotechnology (1994), 12:926-928). miRNA assays based on bDNA signal amplification are commercially available. One such assay is the QuantiGene® 2.0 miRNA Assay (Affymetrix, Santa Clara, Calif.).

Northern Blot and in situ hybridization may also be used to detect miRNAs. Suitable methods for performing Northern Blot and in situ hybridization are known in the art.

Advanced sequencing methods can likewise be used as available. For example, miRNAs can be detected using Illumina® Next Generation Sequencing (e.g., Sequencing-By-Synthesis or TruSeq methods, using, for example, the HiSeq, HiScan. GenomeAnalyzer, or MiSeq systems (Illumina, Inc., San Diego, Calif.)). miRNAs can also be detected using Ion Torrent Sequencing (Ion Torrent Systems, Inc., Gulliford, Conn.), or other suitable methods of semiconductor sequencing.

Mass spectroscopy can also be used to quantify miRNA using RNase mapping. Isolated RNAs can be enzymatically digested with RNA endonucleases (RNases) having high specificity (e.g., RNase TI, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESTMS. The presence of posttranscriptional modifications can be revealed by mass shifts from those expected based upon the RNA sequence. Ions of anomalous mass/charge values can then be isolated for tandem MS sequencing to locate the sequence placement of the posttranscriptionally modified nucleoside.

Matrix-assisted laser desorption/ionization mass spectrometry (MALDI-MS) has also been used as an analytical approach for obtaining information about post-transcriptionally modified nucleosides. MALDI-based approaches can be differentiated from EST-based approaches by the separation step. In MALDI-MS, the mass spectrometer is used to separate the miRNA.

To analyze a limited quantity of intact miRNAs, a system of capillary LC coupled with nanoESI-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nanospray ion source, a Nanovolume Valve (Valco Instruments), and a splitless nano HPLC system (DiNa, KYA Technologies). Analyte/TEAA is loaded onto a nano-LC trap column, desalted, and then concentrated. Intact miRNAs are eluted from the trap column and directly injected into a CI 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple miRNAs can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels.

In certain embodiments, labels, dyes, or labeled probes and/or primers are used to detect amplified or unamplified miRNAs. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miRNA amplification is preferred.

A probe or primer may include standard (A, T or U, G and C) bases, or modified bases. Modified bases include, but are not limited to, the AEGIS bases (from Eragen Biosciences). In certain aspects, bases are joined by a natural phosphodiester bond or a different chemical linkage. Different chemical linkages include, but are not limited to, a peptide bond or a Locked Nucleic Acid (LNA) linkage.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan™) probes, stem-loop molecular beacons, stemless or linear beacons, peptide nucleic acid (PNA) Molecular Beacons, linear PNA beacons, non-FRET probes, Sunrise™/AmplifluorB™ probes, stem-loop and duplex Scorpion™ probes, bulge loop probes, pseudo knot probes, cyclicons, MGB Eclipse™ probe (Epoch Biosciences), hairpin probes, PNA light-up probes, anti-primer quench probes, self-assembled nanoparticle probes, and ferrocene-modified probes.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels. In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g. biotin-avidin). In still other aspects, use of labels can be accomplished using any one of a large number of known techniques employing known labels, linkages, linking groups, reagents, reaction conditions, and analysis and purification methods.

miRNAs can be detected by direct or indirect methods. In a direct detection method, one or more miRNAs are detected by a detectable label that is linked to a nucleic acid molecule. In such methods, the miRNAs may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miRNAs, are detected using FlexMAP Microspheres (Luminex) conjugated with probes to capture the desired nucleic acids. Some methods may involve detection with polynucleotide probes modified with fluorescent labels or branched DNA (bDNA) detection, for example.

In other embodiments, nucleic acids are detected by indirect detection methods. For example, a biotinylated probe may be combined with a streptavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises Phycolink® Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In certain embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups.

In other embodiments, methods relying on hybridization and/or ligation to quantify miRNAs may be used, including oligonucleotide ligation (OLA) methods and methods that allow a distinguishable probe that hybridizes to the target nucleic acid sequence to be separated from an unbound probe. As an example, HARP-like probes may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

A probe ligation reaction may also be used to quantify miRNAs. In a Multiplex Ligation-dependent Probe Amplification (MLPA) technique, pairs of probes which hybridize immediately adjacent to each other on the target nucleic acid are ligated to each other driven by the presence of the target nucleic acid. In some aspects, MLPA probes have flanking PCR primer binding sites. MLPA probes are specifically amplified when ligated, thus allowing for detection and quantification of miRNA biomarkers.

Hematopoietic Stem Cells (HSCs) are able to give rise to all cell types of the hematopoietic compartment, including, without limitation the myeloid lineage, which includes, without limitation, monocytes, macrophages, neutrophils, basophils, eosinophils, erythrocytes, megakaryocytes, platelets, and dendritic cells; and the lymphoid lineage, which includes, without limitation, T-cells. B-cells, NKT-cells, and NK cells.

In some embodiments, the disclosed methods are used to accelerate and monitor hematopoietic compartment reconstitution in HSC transplant recipients. As disclosed herein, HSC transplant recipients may receive a bone marrow transplant, an HSC-enriched bone marrow transplant, a transplant of cord blood, a transplant of HSC-enriched cord blood, a transplant of placenta-derived blood, a transplant of purified or partially-purified HSCs, a transplant of HSCs derived from an HSC cell line, or a transplant of conditionally immortalized HSCs. In such embodiments, HSCs may be administered as a step in the process of an HSC transplantation procedure. As disclosed herein, the HSCs may be included, without limitation, in transplanted bone marrow, transplanted cord blood, or in transplanted cell lines. In certain embodiments, the transplant recipient is a human subject. Suitable HSCs may be obtained by any suitable technique known in the art. For example, HSCs may be found in the bone marrow of a donor, which includes femurs, hip, ribs, sternum, and other bones. Any method known in the art for extracting or harvesting bone marrow cells may be used. In one non-limiting example, HSCs may be obtained directly from the marrow cavity of the hip using a needle and syringe to aspirate cells from the marrow cavity. Rich marrow may be obtained from the hip by performing multiple small aspirations.

HSCs suitable for use with the disclosed methods may be produced from embryonic stem (ES) cells and/or induced pluripotent stem (iPS) cells. Any method of producing HSCs from ES cells and/or iPS cells known in the art may be used. For example, HSCs may be produced from ES cells by patterning the hematopoietic development of ES cell culture on the hematopoietic commitment in the early embryo.

Suitable HSCs may also be obtained from peripheral blood cells found in the blood of a donor, often following pre-treatment with cytokines, such as G-CSF (granulocyte colony-stimulating factors), that induce HSCs to be released from the bone marrow compartment of the donor. HSCs may also be obtained from peripheral blood that has undergone an apheresis procedure to enrich for HSC. Any apheresis procedure known in the art may be used. In certain embodiments, the apheresis procedure is a leukapheresis procedure.

Additionally, suitable HSCs may be obtained from umbilical cord blood, placenta, and mobilized peripheral blood. For experimental purposes, fetal liver, fetal spleen, and AGM (Aorta-gonad-mesonephros) of animals are also useful sources of HSCs. Additionally, HSCs may be procured from a source that obtained HSCs from the bone marrow, peripheral blood, umbilical cord, or fetal tissue of a donor. Alternatively, the HSCs may be included in a bone marrow, peripheral blood, umbilical cord, or fetal tissue sample of a donor.

In some embodiments, human HSCs are obtained from any source, e.g., the bone marrow, umbilical cord, peripheral blood, or fetal tissue of blood, of type A+, A−, B+, B−, O+, O−, AB+, and AB− donors. In other embodiments, human HSCs are obtained from any source, e.g., the bone marrow, umbilical cord, peripheral blood, or fetal tissue of blood, of universal donors or donors having a rare blood type.

In some cases, human HSCs may be obtained by anesthetizing the stem cell donor, puncturing the posterior superior iliac crest with a needle, and performing aspiration of bone marrow cells with a syringe. In some cases, HSCs may be obtained from the peripheral blood of a donor, where a few days prior to harvesting the stem cells from the peripheral blood, the donor is injected with G-CSF in order to mobilize the stem cells to the peripheral blood.

Therefore, in some embodiments, HSCs are obtained from an autologous donor, that is the donor will also be the recipient of the HSCs derived from such HSCs. Any methods known in the art and described herein may be used to obtain HSCs from the autologous donor. The HSCs and/or any therapeutic products derived or produced therefrom are then transplanted, administered, and or transfused back to the original donor. Similarly, HSCs may be obtained from an allogenic donor, such as a sibling, parent, or other relative of a subject in need of an HSC transplantation. In some cases, allogenic HSCs are obtained by collecting HSCs from different blood groups or major histocompatibility complex (MHC) or human leukocyte antigen (HLA) matching sources. Autologous and/or allogenic HSC transplantation may occur at any time after the donation, such as days later, months later, or even years later. Autologous donation may be particularly useful in cases where the subject in need of HSCs would have a negative, deleterious, or toxic reaction to transplantation and/or transfusion of HSCs from any other donor, including allogenic and/or universal donors. Examples of patients that may benefit from autologous and/or allogenic donation are well known in the art and include, without limitation, those suffering from an autoimmune disorder, blood disease or disorder, immune disease or disorder, or other related diseases or conditions.

Cells obtained from, for example, bone marrow, peripheral blood, or cord blood, are typically processed after extraction or harvest. Any method known in the art for processing extracted or harvest cells may be used. Examples of processing steps include, without limitation, filtration, centrifugation, screening for hematopathologies, screening for viral and/or microbial infection, erythrocyte depletion, T-cell depletion to reduce incidence of graft-versus-host disease in allogenic stem cell transplant recipients, volume reduction, cell separation, resuspension of cells in culture medium or a buffer suitable for subsequent processing, separation of stem cells from non-stem cells e.g., stem cell enrichment), ex vivo or in vitro stem cell expansion with growth factors, cytokines, and/or hormones, and cryopreservation.

HSCs obtained from a donor may be identified and/or enriched by any suitable method of stem cell identification and enrichment known in the art, such as by utilizing certain phenotypic or genotypic markers. For example, in some embodiments, identification of HSCs includes using cell surface markers associated with HSCs or specifically associated with terminally differentiated cells of the system. Suitable surface markers may include, without limitation, one or more of c-kit, Sca-1, CD4, CD34, CD38, Thy1, CD2, CD3, CD4, CD5, CD8. CD43, CD45, CD59, CD90, CD105, CD133, CD135, ABCG2, NK1.1, B220, Ter-119, Flk-2, CDCP1, Endomucin, Gr-1, CD46, Mac-1, Thy1.1, and the signaling lymphocyte activation molecule (SLAM) family of receptors. Examples of SLAM receptors include, without limitation, CD150, CD48, and CD244. Any suitable method for stem cell enrichment known in the art may be used. Examples of stem cell enrichment methods include, without limitation, fluorescence activated cell sorting (FACS) and magnetic activated cell sorting (MACS).

Accordingly, HSCs suitable for use in any of the disclosed methods may be obtained from bone marrow, from an apheresis procedure, from peripheral blood cells, from peripheral blood cells that have undergone leukapheresis, from umbilical cord blood, from amniotic fluid, from cultured HSC cells, from an immortalized HSC cell line, or from a conditionally immortalized HSC cell line. Alternatively, HSCs suitable for use in any of the methods of the present disclosure may be present in bone marrow, in peripheral blood cells, in peripheral blood cells that have undergone leukapheresis, in umbilical cord blood, in amniotic fluid, and in cell lines.

In further embodiments, HSC-containing compositions and populations of HSCs of the present disclosure are administered to a subject in need of hematopoietic stem cell (HSC) transplantation as a step in the process of an HSC transplantation procedure. In certain embodiments, the subject is a human patient in need of a HSC transplant. In other embodiments, the subject is any non-human animal, including, without limitation, laboratory/research animals, rodents, pets, livestock, farm animals, work animals, pack animals, rare or endangered species, racing animals, zoo animals, monkeys, primates, mice, rats, guinea pigs, hamsters, dogs, cats, horses, cows, pigs, sheep, goats, and chickens.

The HSC transplantation procedure may be a myeloablative HSC transplant. Myeloablation generally refers to the ablation or suppression of the endogenous hematopoietic compartment of an HSC transplant recipient. Myeloablation occurs prior to HSC transplantation. In HSC transplant recipients suffering from a hematological disease, such as a hematological cancer, myeloablation may be performed to help eradicate the disease. Myeloablation may also be performed to suppress the endogenous immune system of the HSC transplant recipient in order to help reduce the risk of rejection of the transplanted HSCs (e.g., graft-versus-host disease). Any method known in the art for myeloablation may be used. Examples of myeloablation procedures include, without limitation, chemotherapy, irradiation, and combinations thereof.

Alternatively, the HSC transplantation procedure may be non-myeloablative. In non-myeloablative procedures lower doses of chemotherapy and/or radiation are used in the recipient prior to HSC transplantation.

Subjects in need of an HSC transplant include subjects presenting with an HSC transplant indication. Examples of HSC transplant indications include, without limitation, a hematological malignancy, a myeloma, multiple myeloma, a leukemia, acute lymphoblastic leukemia, chronic lymphocytic leukemia, a lymphoma, indolent lymphoma, non-Hodgkin lymphoma, diffuse B cell lymphoma, follicular lymphoma, mantle cell lymphoma, T cell lymphoma, Hodgkin lymphoma, a neuroblastoma, a retinoblastoma, Shwachman Diamond syndrome, a brain tumor, Ewing's Sarcoma, a Desmoplastic small round cell tumor, a relapsed germ cell tumor, a hematological disorder, a hemoglobinopathy, an autoimmune disorder, juvenile idiopathic arthritis, systemic lupus erythematosus, severe combined immunodeficiency, congenital neutropenia with defective stem cells, severe aplastic anemia, a sickle-cell disease, a myelodysplasia syndrome, chronic granulomatous disease, a metabolic disorder, Hurler syndrome, Gaucher disease, osteopetrosis, malignant infantile osteopetrosis, heart disease, HIV, and AIDS. Additionally, a subject in need of an HSC transplant can also include a subject that has had an organ transplant.

As disclosed herein, comparative analysis of cell-free miR-150 can allow evaluation of the effectiveness of myeloablative conditioning. This can therefore serve as surrogate for absolute neutrophil count (ANC) in making therapeutic decisions, such as time for infusion and grafting efficiency after HSC transplant. miR-150 depletion kinetics can also identify patients who cannot tolerate full-dose of 3 or 4 day (12 Gy total) total meyloablative radiation. miR-150 can be used for evaluation of myeloablation in patients receiving cytotoxic drugs such as cysplatin, doxorubicin, and 5-FU. miR-150 levels can also be used to evaluate the effect of growth factors such as GM-CSF and G-CSF (Neupogen, filgrastim) administered in transplant patients to enhance immune recovery and marrow reconstitution.

In some embodiments, the ratio of miR-302d-3p/miR-150-5p or miR-23a miR-150-5p can be used for evaluation of myeloid suppression and reconstitution. miR-23a/miR-223-3p ratio can provide readout of platelet recovery after transplant. The miR-155-5p/miR-150 comparison can allow early evaluation of GVHD. In some embodiments, the basal unaltered level of miR-155 indicates absence of acute GVHD. In some embodiments, the progressive miR-21/miR-150 and miR-29a/miR-150 ratio indicate acute lung inflammation.

Increase in serum/plasma levels of miR-142-3p, miR-144-3p, miR-126-3p, miR-191-5p, let-7b-5p, let-7g-5p, let-7a-5p, (normalized with miR-302d-3p, miR miR-130b-3p or miR-23a) in the later stages during fractionated radiation or within days/weeks after completion of the course can predict potentially lethal pulmonary toxicity and can be used for making go/no-go (to treat or not-to treat) decisions. These can further allow modifying the dose and regimen as conventional fractionated radiation could take 6 weeks or more to complete. These can also help deciding administration of prophylactics such as corticosteroids (prednisone) to prevent pneumonitis and angiotensin converting enzyme inhibitors (ACEI) and hydroxymethylglutaryl coenzyme A (HMG-CoA) reductase inhibitors (statins) to prevent or reduce pulmonary fibrosis. These biomarkers could help evaluate the effect of the mitgators of the damage and injury in animal models. Increase in serum levels of miR-21 and miR-29a (normalized with miR-302d-3p, miR miR-130b-3p or miR-23a) are early biomarkers of lung inflammation detectable 2 weeks after acute single dose and 4 weeks after 6×2 Gy (3 day) fractionated complete myeloablative radiation. These can help treatment planning/therapy guiding during conventional fractionated radiation or when high dose SBRT protocols are used to treat lung cancer patients. miR-146a and miR-192 (e.g. normalized with miR-302d-3p, miR miR-130b-3p or miR-23a) in serum are indicators of acute lung inflammation (pneumonitis) and therefore can serve as biomarkers to decide on timing, dose and course of corticosteroids. miR-21, miR-29a and miR-192 (e.g. normalized with miR-302d-3p, miR miR-130b-3p or miR-23a) are serum biomarkers of pulmonary fibrosis and therefore can help in guiding therapy. The treatment option here includes administration of Corticosteroids (prednisone), Cyclophosphamide (Cytoxan®): N-acetylcysteine (NAC), or supplemental oxygen therapy. The markers can also help evaluating the efficacy of above treatments.

It must be noted that as used herein and in the appended claims, the singular forms "a." "an," and "the" include plural referents unless the context clearly dictates otherwise. Thus, for example, reference to "a peptide" includes a plurality of such peptides, reference to "the peptide" is a reference to one or more peptides and equivalents thereof known to those skilled in the art, and so forth.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that the throughout the application, data are provided in a number of different formats, and that these data represent endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "radiation injury" refers to an injury or damage that is caused by exposure to ionizing radiation. Radiation injury includes but is not limited to radiation poisoning, radiation sickness, acute radiation syndrome or chronic radiation syndrome.

The term "ionizing radiation" refers to radiation that has sufficient energy to eject one or more orbital electrons from an atom or molecule (e.g. α particles, β particles, γ rays, x-rays, neutrons, protons and other particles having sufficient energy to produce ion pairs in matter).

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder, preventative treatment, that is, treatment directed to minimizing or partially or completely inhibiting the development of the associated disease, pathological condition, or disorder, and supportive treatment, that is, treatment employed to supplement another specific therapy directed toward the improvement of the associated disease, pathological condition, or disorder.

The term "hematopoietic compartment" refers to the cell compartment in a subject that contains all blood cell lineages, including without limitation, the myeloid lineage, which includes, without limitation, monocytes, macrophages, neutrophils, basophils, eosinophils, erythrocytes, megakaryocytes, platelets, and dendritic cells; and the lymphoid lineage, which includes, without limitation, T-cells, B-cells, NKT-cells, and NK cells. The "hematopoietic compartment" can contain all immature, mature, undifferentiated, and differentiated white blood cell populations and sub-populations, including tissue-specific and specialized varieties.

The term "hematopoietic compartment cell formation" in a subject refers to the production and/or expansion of one or more cells of any blood cell lineages of the hematopoietic compartment in the hematopoietic compartment from hematopoietic stem cell (HSC) differentiation, HSC proliferation, and/or HSC survival. "Hematopoietic compartment cell formation" may be the result of HSC engraftment by exogenous HSCs, such as hematopoietic compartment reconstitution in an HSC transplant recipient. Alternatively, "hematopoietic compartment cell formation" may be the result of endogenous HSC differentiation, endogenous HSC proliferation, and/or endogenous HSC survival, such as from hematopoietic compartment autoreconstitution in a subject. In some embodiments, "hematopoietic compartment cell formation" includes, without limitation, one or more of myeloid lineage formation, myeloid lineage progenitor cell formation, monocyte cell formation, macrophage cell formations, neutrophil cell formation, basophil cell formation, eosinophil cell formation, erythrocyte cell formation, megakaryocyte cell formation, platelet cell formation, dendritic cell formation, lymphoid lineage formation, lymphoid lineage progenitor cell formation. T-cell formation, B-cell formation, NKT-cell formation, and NK cell formation.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Identification of Sensitive Serum microRNA Biomarkers for Radiation Biodosimetry microRNAs (miRNAs) are non-coding RNAs of 19-22 nucleotides that were originally identified as regulators of gene expression by inducing cleavage of their target mRNA or blocking translation through base pairing to partially complementary sequences [Bartel D P (2004) Cell 116: 281-297]. miRNAs regulate diverse cellular processes including development, proliferation and differentiation, as well as various disease progressions [Iorio M V, et al. (2012) EMBO Mol Med 4:143-159]. In addition to their roles in post-transcriptional gene regulation, miRNAs in body fluids are proposed and have been assessed as biomarkers for various physiological responses and pathological stages [Cui W, et al. (2011) PLoS ONE 6: e22988; Scholl V, et al. (2012) Leuk Res 36:119-121; Qi P, et al. (2011) PLoS ONE 6: e28486; Weiland M, et al. (2012) RNA Biol 9: 850-859; Cortez M A, et al. (2011) Nat Rev Clin Oncol 8: 467-477; Russo F, et al. (2012) PLoS ONE 7: e47786]. Earlier studies have detected miRNAs in a range of body fluids such as serum, plasma and urine, and miRNAs are relatively stable due to their smaller size and being protected in exosomes [Hunter M P. et al. (2008) PLoS ONE 3:e3694; Valadi H, et al. (2007) Nat Cell Biol 9: 654-659]. However, the current PCR based methods used for evaluation of miRNA in body fluids have limitations. Because several miRNAs are present in low quantities. PCR based detection and quantification often requires pre-amplification of the template and a higher number of amplification cycles, which compromises the reliability of the measurements [Etheridge A, et al. (2011) Mutat Res 717: 85-90]. To circumvent this problem, a digital amplification-free quantification and comparison method was used [Geiss G K, et al. (2008) Nat Biotechnol 26: 317-325] which allowed evaluation of the relative abundance of individual miRNAs in the serum samples and development of a panel of sensitive biomarkers for radiation biodosimetry.

Materials and Methods

Animal Studies

For animal studies involving acute single dose exposure, 8-9 week old *Mus musculus* were used. Male inbred mice (Strains CBA/J and C57BL/6, Jackson Laboratories) were co-housed (five per standard cage) and fed ad libitum. Mice were exposed to total body gamma radiation (TBI) using GammaCell®40 irradiator (Cesium 2137 Source) at a dose rate of 1.1 Gy/min). For each radiation dose (0, 1, 2, 4, 6 and 8 Gy) and time point (24 and 48 hrs) a minimum of five animals were used. Control animals were sham-exposed. For investigating the effect of fractionated dose, 15 animals were exposed to X-rays (in 2 Gy fractions) from a RS-2000

Biological Irradiator at a dose rate of 1 Gy/min. All the animal experiments were done with strict adherence to the institutional guidelines established and approved by the Ohio State University Animal Care and Use Committee (Permit number: 2011A00000029).

Blood was collected by submandibular bleeding or by cardiac puncture. Following coagulation (1 hr at room temperature), serum was separated using microtainer tubes (BD Biosciences) by centrifugation at 10,000 g for 10 min, and then frozen at −80° C. RNA was extracted using the Qiagen miRNA easy kit following the manufacturer's protocol. miRNAs were isolated from serum samples collected from 4-5 animals for each time points, and samples with high levels of hemolysis were excluded from analysis. In a typical isolation procedure, 100 ml serum was used. After lysis using QIAzol reagent, 4-20 pg synthetic oligonucleotides (spike-in oligos) Osa-miRNA-414, Cel-miRNA-248, At-miRNA-159a (Integrated DNA Technologies) were added prior to extraction. RNA was eluted in 100 ml water and concentrated to 20 ml and 3 ml was used for each assay for profiling using nanoString™ Technologies' multiplexed nCounter® platform. The platform incorporates fluorescent barcodes together with a digital readout for single-molecule imaging [Geiss G K, et al. (2008) Nat Biotechnol 26: 317-325]. It does not involve reverse transcription; instead the technology relies on sequence-specific probes to digitally measure miRNA abundance. This hybridization based amplification-free method allows processing of multiple samples, comparing and quantifying the number of molecules even of low abundance. The spike-in oligos allow a volume and quantity based normalization for detection of even small changes in individual miRNAs.

miRNA Expression Profiling

The digital multiplexed nanoString™ nCounter® mouse miRNA expression assay (nanoString™ Technologies) was performed with 10-30 ng total RNA isolated from a net volume of 20 ml serum as input material. Small RNA samples were prepared by ligating a specific DNA tag (miR-tag) onto the 39 end of each mature miRNA according to the manufacturer's instruction. These tags serve several purposes: they normalize the wide range of melting temperatures (Tms) of the miRNAs, provide a template to facilitate the use of the nanoString™ dual probe system, enable single base pair discrimination and specificity of highly homologous miRNA family members, and identify each miRNA species. Excess tags were removed by restriction digestion at 37° C. Hybridizations were carried out by combining 5 ml of each miRNA-miRTag sample with 20 ml of nCounter® Reporter probes in hybridization buffer and 5 ml of nCounter® Capture probes (for a total reaction volume of 30 ml) overnight at 65 uC for 16-20 hrs. Excess probes were removed using two-step magnetic bead based purification on the nCounter® Prep Station (NanoString Technologies). Abundances of specific target molecules were quantified on the nCounter® Digital Analyzer by counting the individual fluorescent barcodes and assessing the target molecules. For each assay, a high-density scan encompassing 600 fields of view was performed. The data was collected using the nCounter® Digital Analyzer after taking images of the immobilized fluorescent reporters in the sample cartridge with a C(CD camera.

Data Analysis miRNA data analysis was performed using the nSolver™ software analysis, freely available from NanoString Technologies. The serum miRNA profiling data was normalized using the average signals obtained from three spike-in oligos, and miRNAs that gave significant hybridization signals were used for downstream analysis. ANOVA was performed with a cutoff p-value of 0.05 to identify a set of miRNAs that had the highest difference in means across samples. Coefficient of variance across samples was also performed with a cutoff of 0.4 and overlapping sets of miRNAs from the above two methods were selected as the most significant set. R software was used for the analysis.

Results

Optimization of Methods for Quantitative Analysis of Serum miRNAs

Figure 1B:
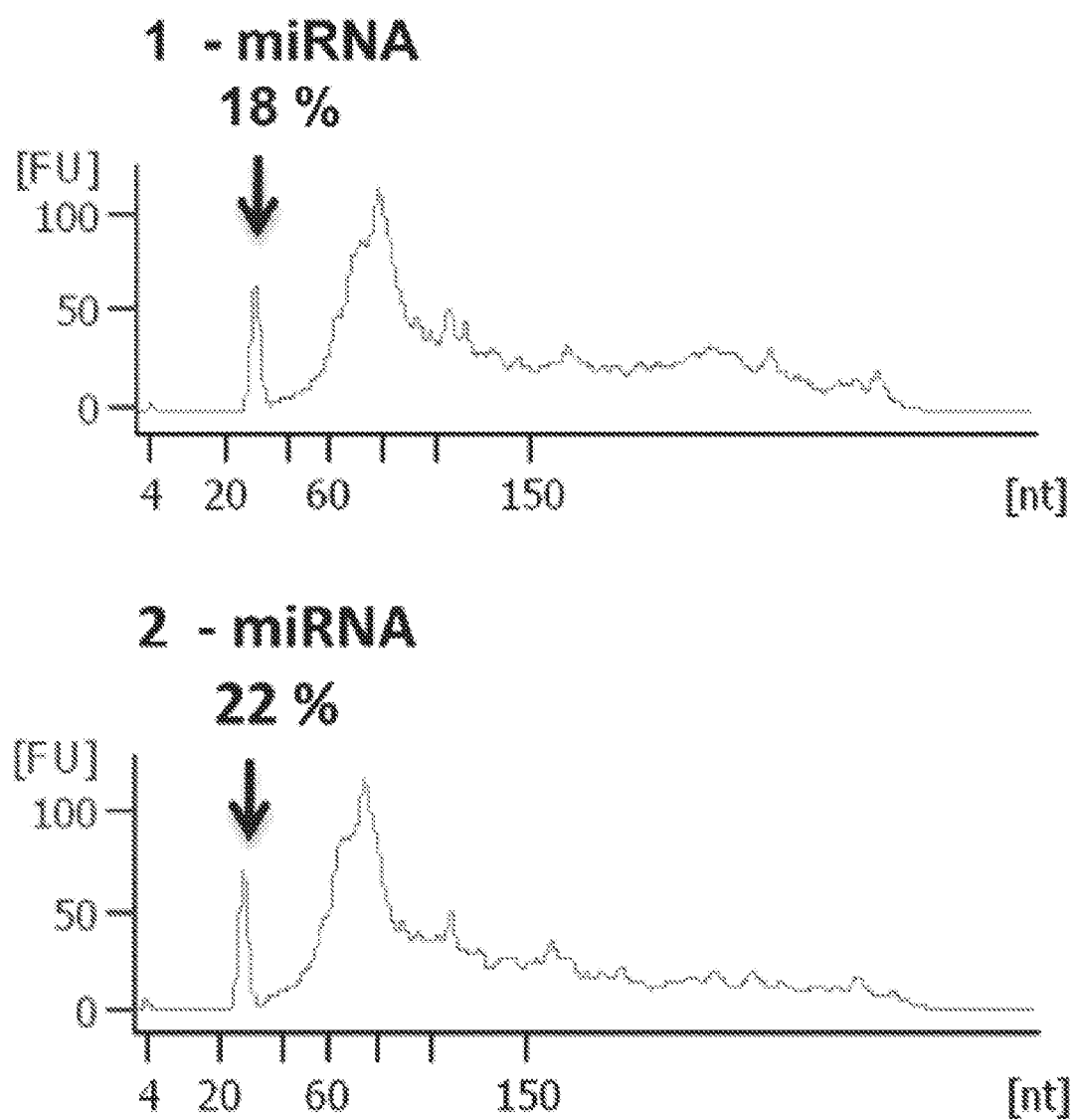
FIG. 1B shows densitometry traces used to quantify and compare the relative abundance of various small RNAs.

The digital multiplexed nanoString™ nCounter® mouse miRNA expression assay was performed on total RNA isolated from 20 ml of serum usually containing a total amount of 10-30 ng of RNA. The nCounter® multiplex platform is capable of detecting approximately 600 mouse specific miRNAs, four housekeeping genes and three non-mammalian miRNAs: Osa-miRNA-414, CelmiRNA-248 and At-miRNA-159a. During RNA isolation, synthetic oligonucleotides (spike-in oligos) corresponding to OsamiRNA-414, Cel-miRNA-248 and At-miRNA-159a were included as controls allowing the normalization of samples. The amounts of spike-in oligos were optimized by comparing their counts with that of endogenous miRNAs in serum samples. The optimal amount of spike-in oligos for normalization was identified to be 0.5-2 pg in each reaction. The inclusion of probes hybridizing to the house keeping genes enabled further identification and separate preparations with cellular RNA contaminations. The optimized method allowed detection of changes in serum miRNAs that are specific to changes in physiological and treatment conditions, such as response to radiation. The purity and integrity of the RNA recovered from serum samples was validated on a small RNA bioanalyzer (FIG. 1A). miRNAs were found to represent 18-22% of total serum RNA preparations (FIG. 1B).

Figure 2C:
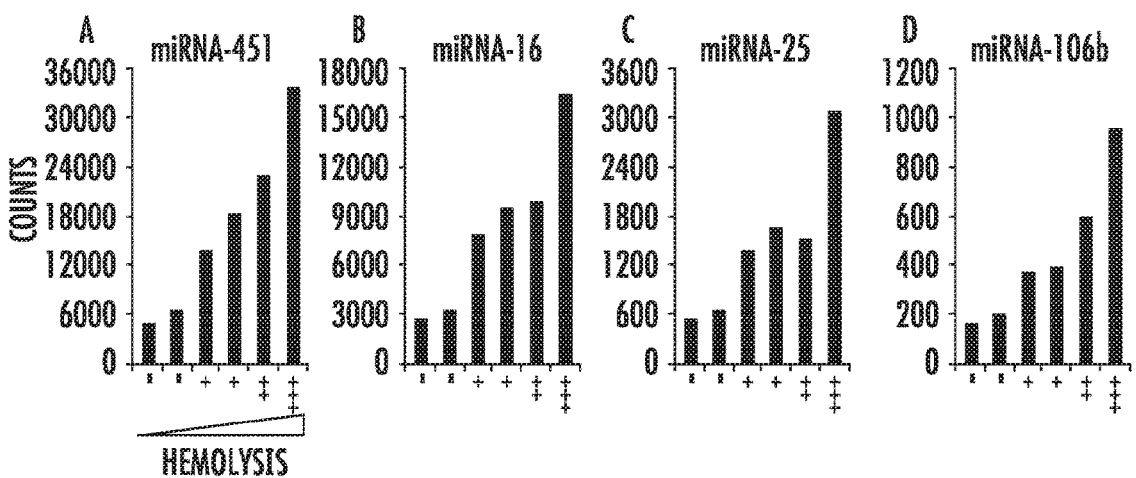
FIG. 2C is a partial list of miRNAs detected in rhesus monkey serum.
Figures 3A, 3B, 3C, 3D, 3E, 3F, 3G, 3H:
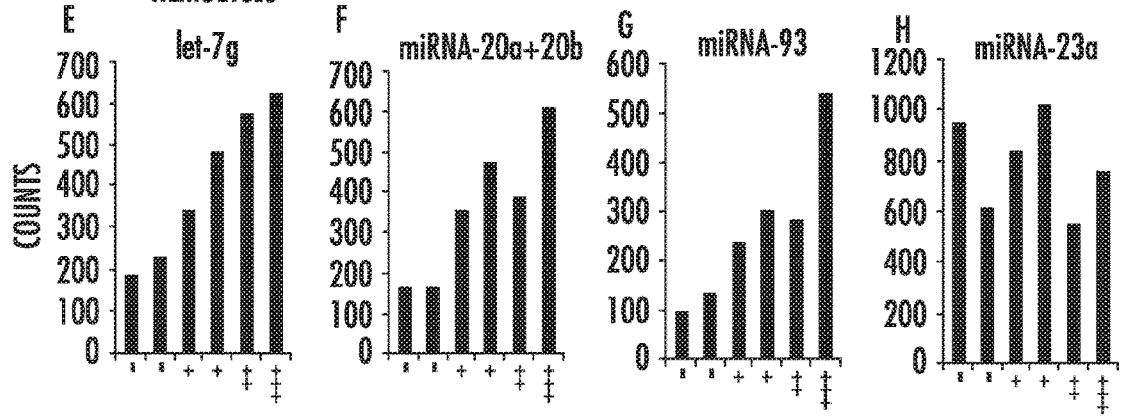
FIGS. 3A to 3H are a series of bar graphs measuring levels (counts) of miRNA-451 (FIG. 3A), miRNA-16 (FIG. 3B), miRNA-25 (FIG. 3C), miRNA-106b (FIG. 3D), let-7g (FIG. 3E), miRNA-20a+20b (FIG. 3F), miRNA-93 (FIG. 3G), and miRNA-23a (FIG. 3H) derived from red blood cells as a function of increasing levels (+) of hemolysis.

The nCounter® expression profiling conducted on total RNA isolated from mice serum samples identified 88 miRNAs with high confidence. miRNA-451 was found to be the most abundant in serum preparations, contributing to 22-23% of total miRNAs (FIG. 2). miRNA-16 ranked second, representing, 13%. Analysis of serum samples from a minimum of three animals from each of the two strains of mice (CBA/J and C57BL/6) showed similar results. Several evolutionarily conserved and functionally significant miRNAs, such as miRNA-150, miRNA-21, miRNA-29a and miRNA-23a, were also detected in serum samples [Wang B, et al. (2012) Hepatology 56: 186-197; Thum T, et al. (2008) Nature 456: 980-984; Teichler S, et al. (2011) Blood 118: 1899-1902; Vasilescu C, et al. (2009) PLoS ONE 4: e7405; Zhou B, et al. (2007) Proc Natl Acad Sci USA 104: 7080-7085]. Given the abundance of miRNA-451 and miRNA-16 in serum, feasibility of using these as endogenous normalizers was investigated the by comparing their signals with that of spike-in oligos. However, because of the abundance of these miRNAs in red blood cells, even a small level of hemolysis was found to skew the results. Therefore, these endogenous markers were not used as biological normalizers. Furthermore, comparison of samples with increasing levels of hemolysis enabled identification of additional markers that potentially originating from the lysis of red blood cells. These include miRNA-25, miRNA-106b, let-7g, and miRNA-93 (FIG. 3), while the level of miRNA-23a was not increased in samples with higher levels of hemolysis. Thus, parallel analysis of samples normalized with multiple controls allowed identification of markers that are specific and sensitive to radiation treatment.

Radiation Dose Dependant Changes in Serum miRNA Profile Following Single Acute Dose Using the nCounter® multiplex assay, miRNAs in serum samples from control and irradiated animals collected 24 hrs after 1, 2, 4, 6 and 8 Gy total body irradiation (TBI) were compared. In order to minimize experimental error, irradiation, serum collection, RNA isolation, miRNA profiling, and normalization were done in parallel with controls and treatment groups. Samples with traces of cellular RNA contamination (with counts of 30 or above for any of the four housekeeping genes) were excluded from the analysis. Samples with high levels of hemolysis observed visually or based on relative abundance of miRNA-451 (23%), miRNA-16 (13%) correlating with increase in miRNA-25, miRNA-106b, let-7 g and miRNA-93 were also excluded from analysis.

Figure 4A:
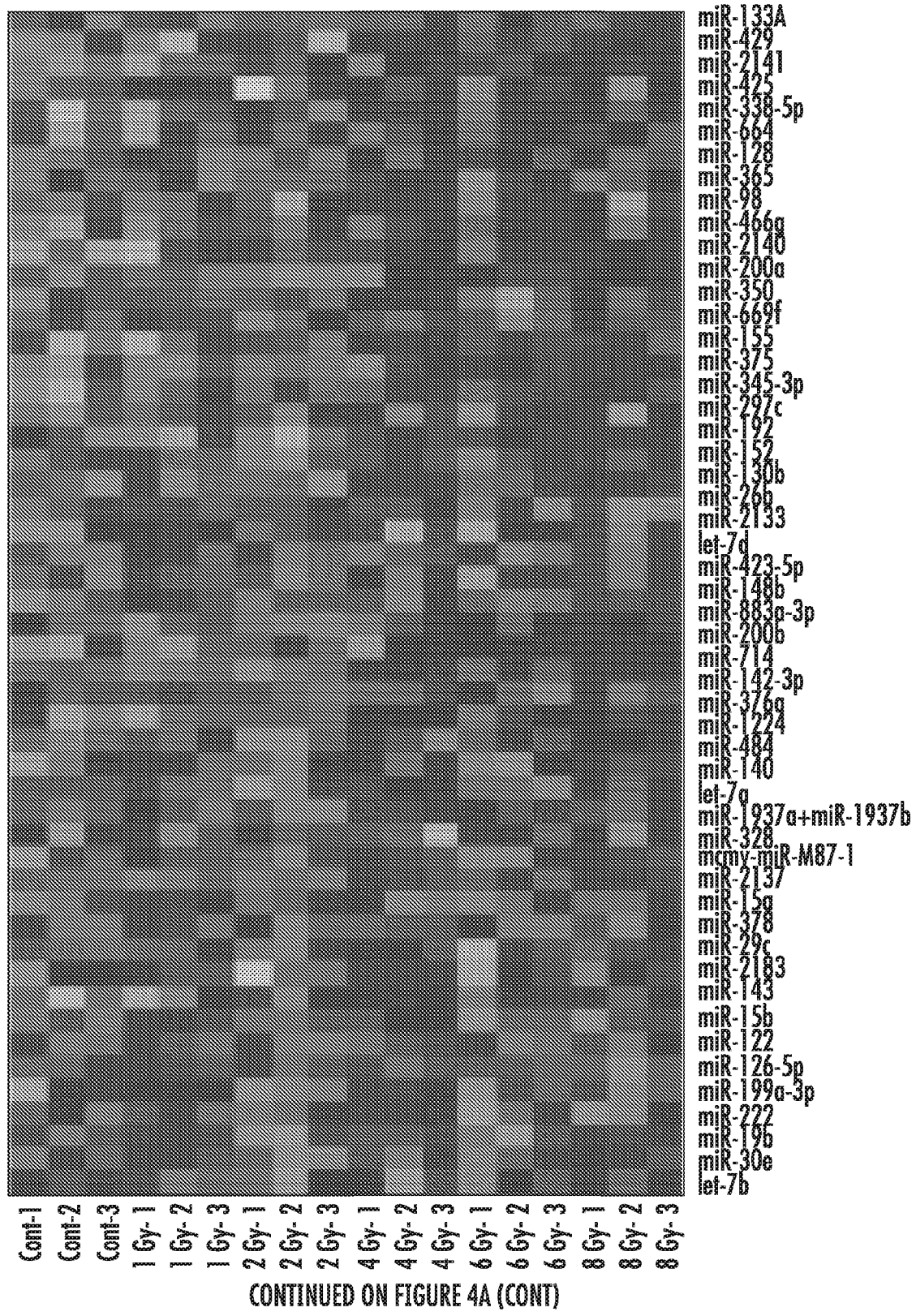
FIG. 4A is a heat map generated from the actual counts for 88 miRNAs detected in serum.
Figure 4A:
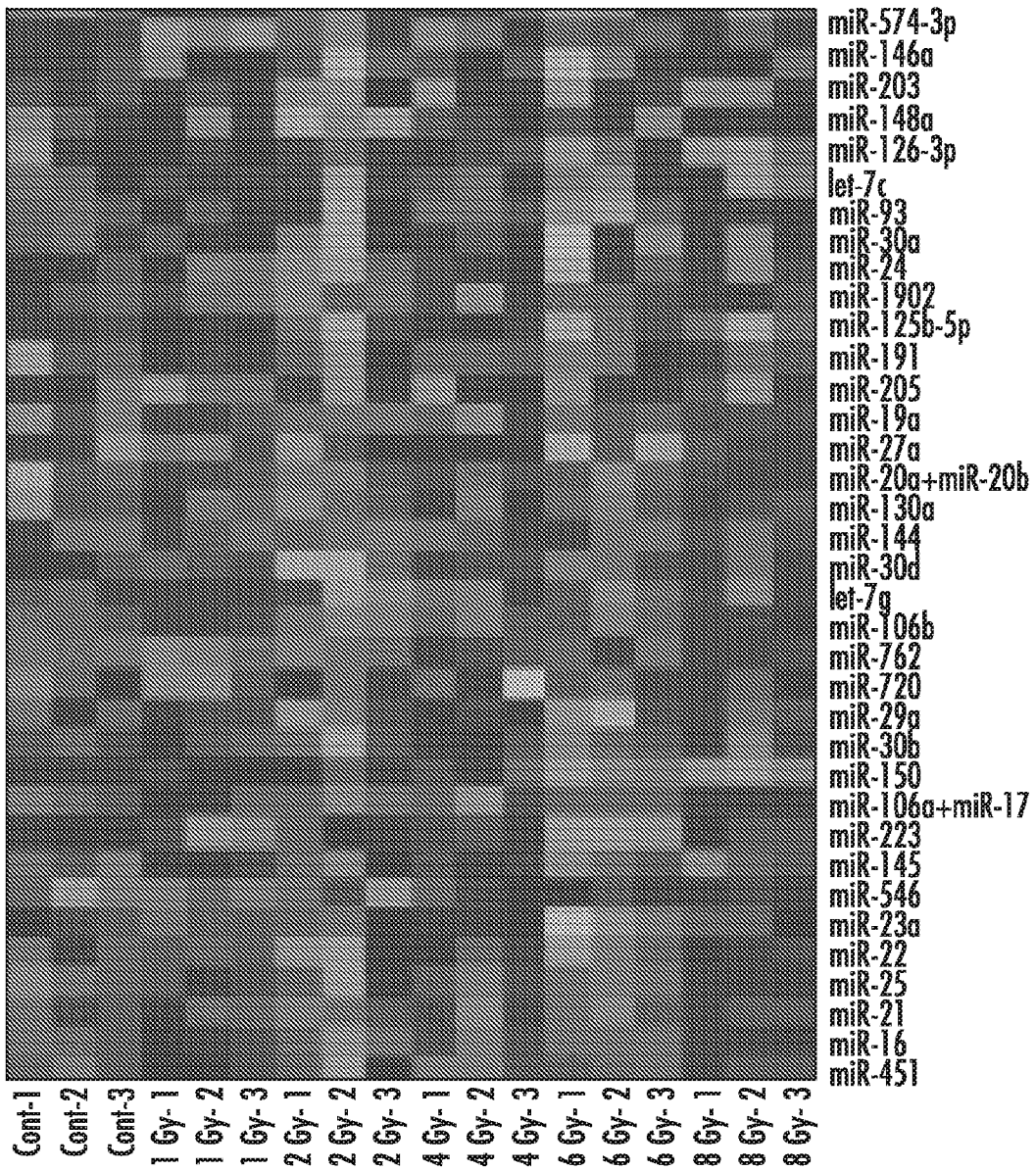
Figure 4B:
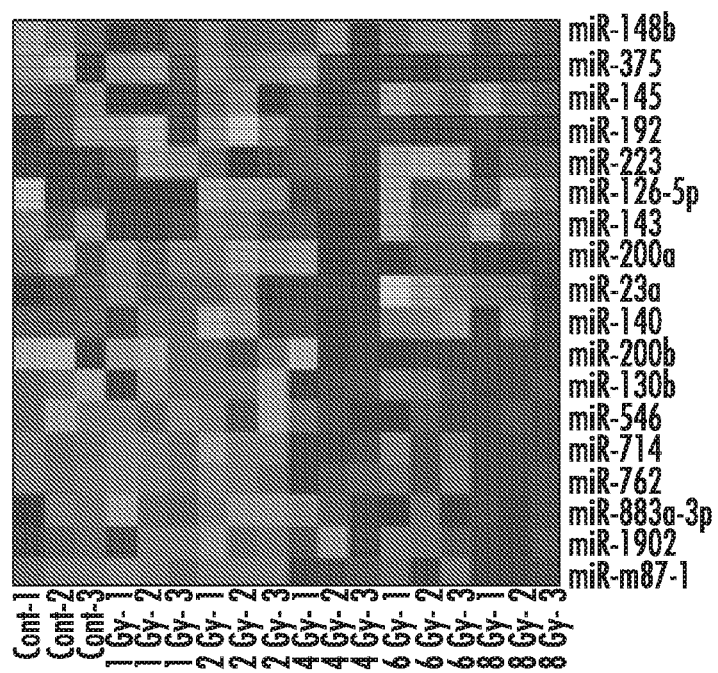
FIG. 4B is a heat map showing variations in a panel of 18 radio-responsive miRNAs, identified by ANOVA with a cutoff p-value of 0.05.
Figure 4C:
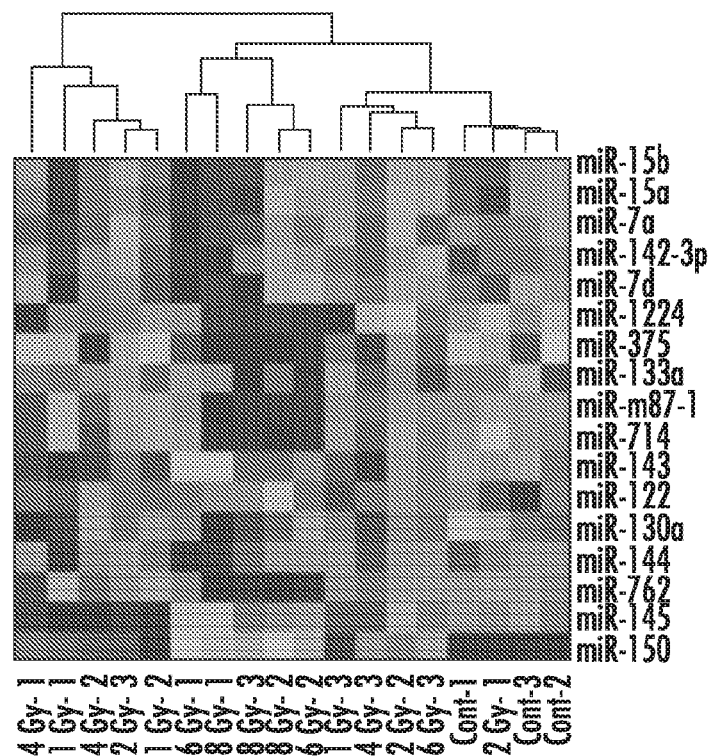
FIG. 4C is a dendrogram with a panel of markers identified with coefficient of variance across samples with a cutoff value of 0.4.
Figure 4D:
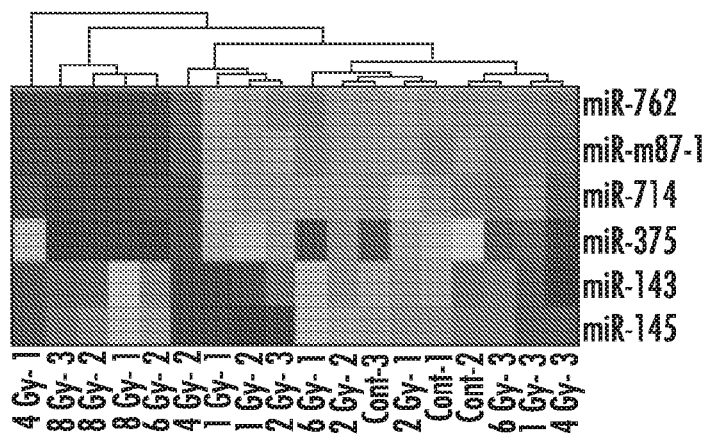
FIG. 4D is a heat map showing an overlapping set of miRNAs from ANOVA and CV.

The relative changes of 88 miRNAs detected in serum samples were evaluated for their radiation dose dependent changes (FIG. 4A). Changes were observed in several miRNAs distinguishable from irradiated versus controls and between different doses of radiation (FIG. 4B). At first, ANOVA was performed with a cutoff p-value of 0.05 to identify a set of miRNAs that had the highest difference in means across samples. Next, the coefficient of variance was calculated with a cutoff of 0.4 (FIG. 4C). Finally, an overlapping set of miRNAs from the above two methods was selected as the most significant and responsive set (FIG. 4D). Several markers were found clustering with specific dose or dose range indicating a clear radiation biodosimetry potential.

Figures 5A, 5B, 5C, 5D:
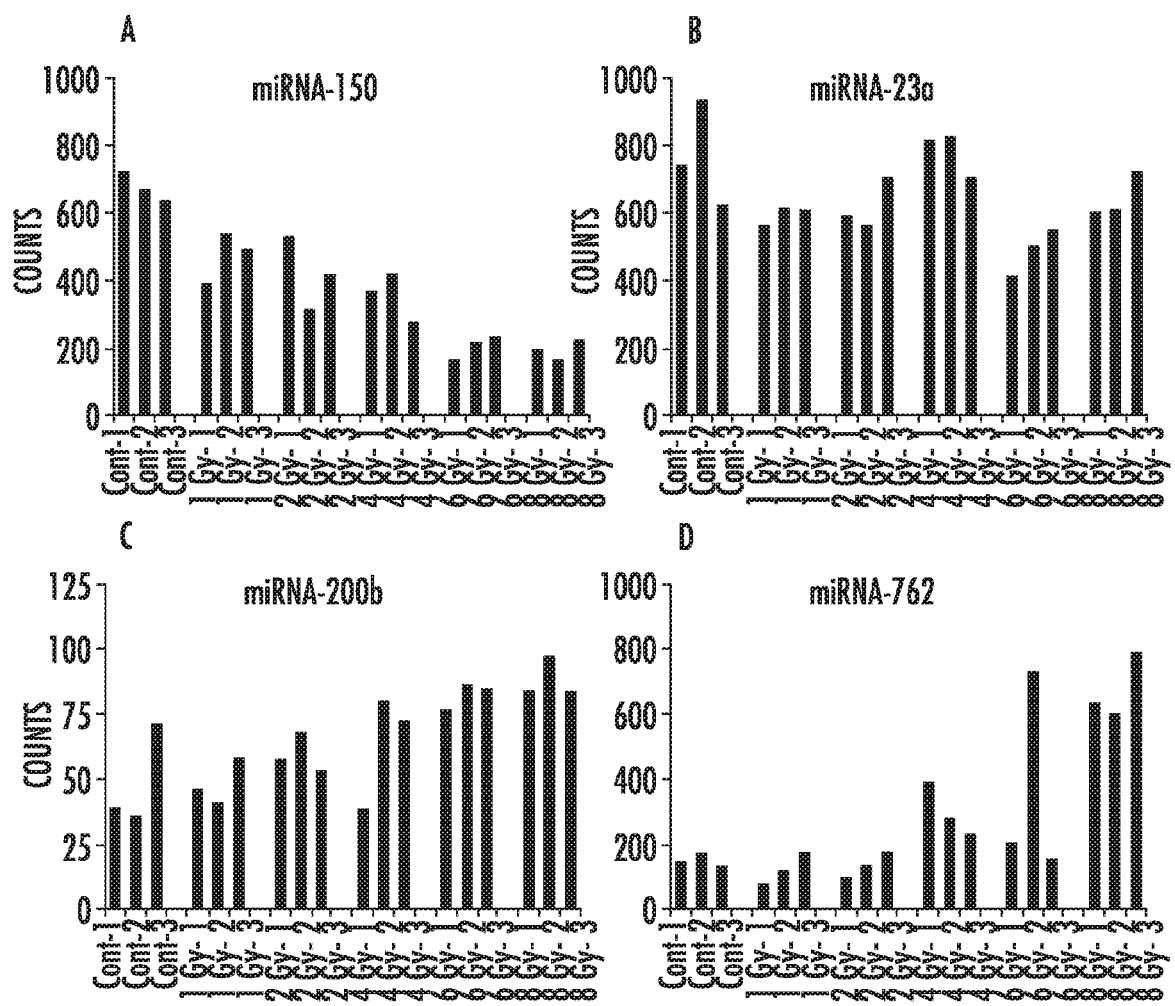
FIGS. 5A to 5D are bar graphs showing analysis of fold variations of selected serum miRNA biomarkers with a clear dose response. Histograms show variations in the fluorescent counts detected in the nCounter® multiplex assay, plotted against treatment. The counts obtained after normalization using multiple spike-in oligos were plotted for individual animals.
Figures 6A, 6B, 6C:
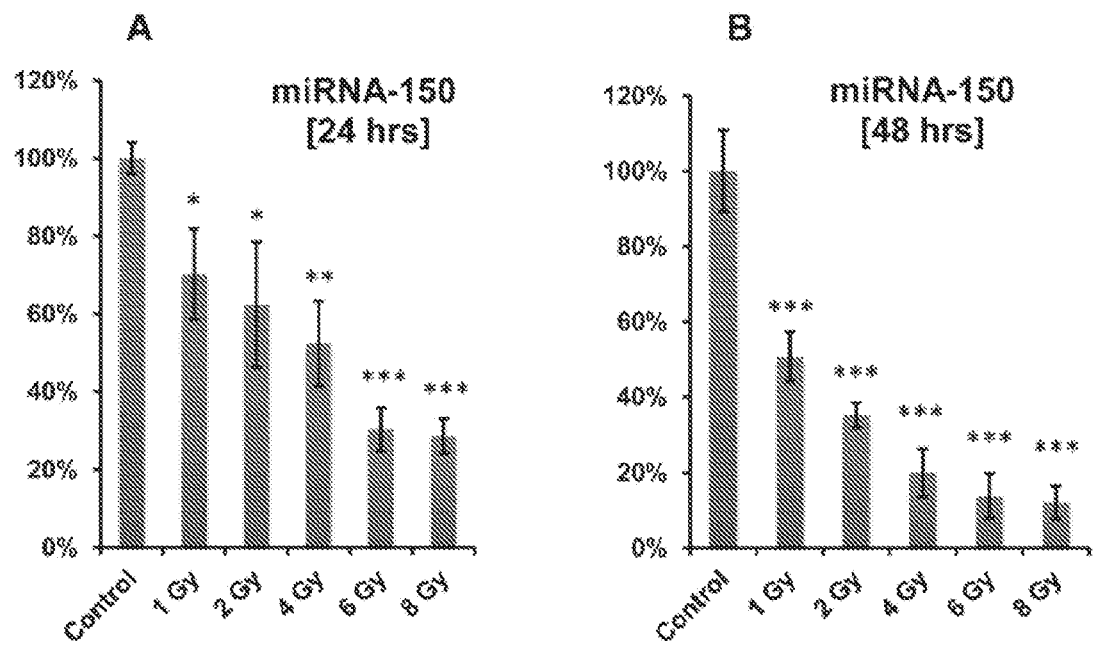
FIGS. 6A and 6B show dose and time dependent depletion of miRNA-150 in animals exposed to 1, 2, 4, 6 and 8 Gy with reference to controls analyzed at 24 hrs (FIG. 6A) and 48 hrs (FIG. 6B). Statistical analysis was performed using an unpaired two-tailed students t-test (*)=$p<0.05$; ()=$p<0.005$; (*)=$p<0.0005$.
FIG. 6C shows kinetics of depletion of miRNA-150 as a function of dose and time relative to respective controls.

Selected radiosensitive miRNAs identified from cluster analysis were further investigated for their dose and time dependent changes. In order to evaluate the robustness of the response of each individual marker, the normalized fluorescence counts from individual animals that received varying doses of radiation was plotted (FIG. 5). miRNA-150 was identified as a robust radio-responsive serum biomarker, with a clear dose response in all animals compared 24 hrs after radiation (FIG. 5A). A decrease in levels of miRNA-150 was evident even in animals that received 1 Gy radiation, which further decreased with increasing dose (2, 4, 6 and 8 Gy). Molecules that exhibited an increase in their serum levels after radiation exposure include miRNA-200b and miRNA-762, and these changes were more pronounced in animals that received higher doses (FIG. 5C, 5D). miRNA-23a, whose counts in controls are comparable to that of miRNA-150, was used as another control (FIG. 5B).

miRNA-150 was further investigated for its kinetics of depletion by comparing the dose response at 24 and 48 hrs. A 30% reduction in serum miRNA-150 was observed in animals 24 hrs after 1 Gy total body radiation exposure, which further decreased to 50% by 48 hrs (FIG. 6). A time and dose dependent decrease in serum miRNA-150 was evident with an increase in dose, where a gradual decrease in counts was observed with increasing dose. This further confirms the sensitivity and robustness of this serum marker as a candidate for radiation biodosimetry.

Dose and Time Dependant Changes in miRNAs after Fractionated Radiation Exposure

Figure 7A:
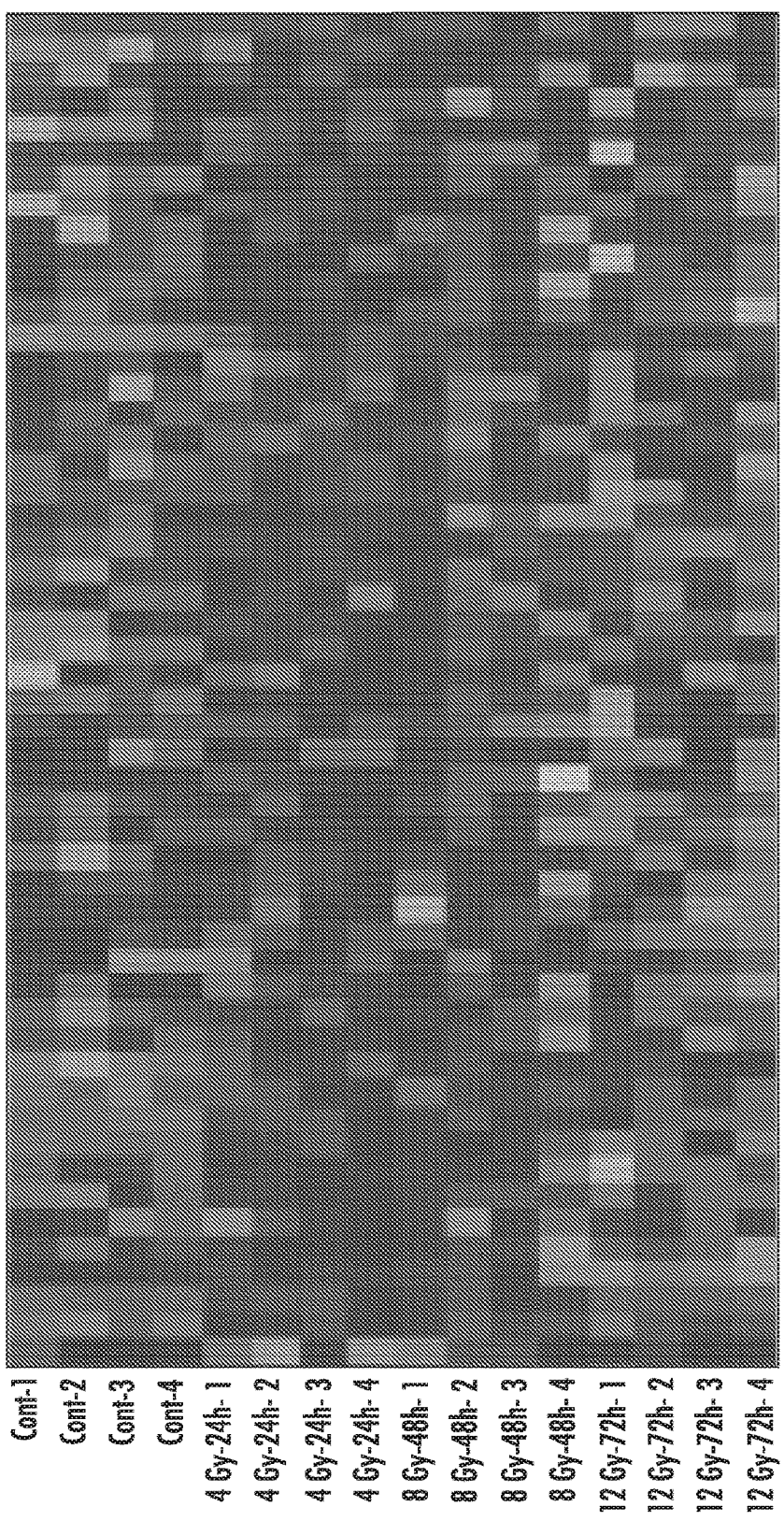
FIG. 7A is a heat map generated using the normalized data for 88 miRNAs detected in serum from four each of control and irradiated animals collected 24 hrs (2×2 Gy=4 Gy), 48 hrs (4×2=8 Gy) and 72 hrs (6×2 Gy=12 Gy).
Figure 7A:
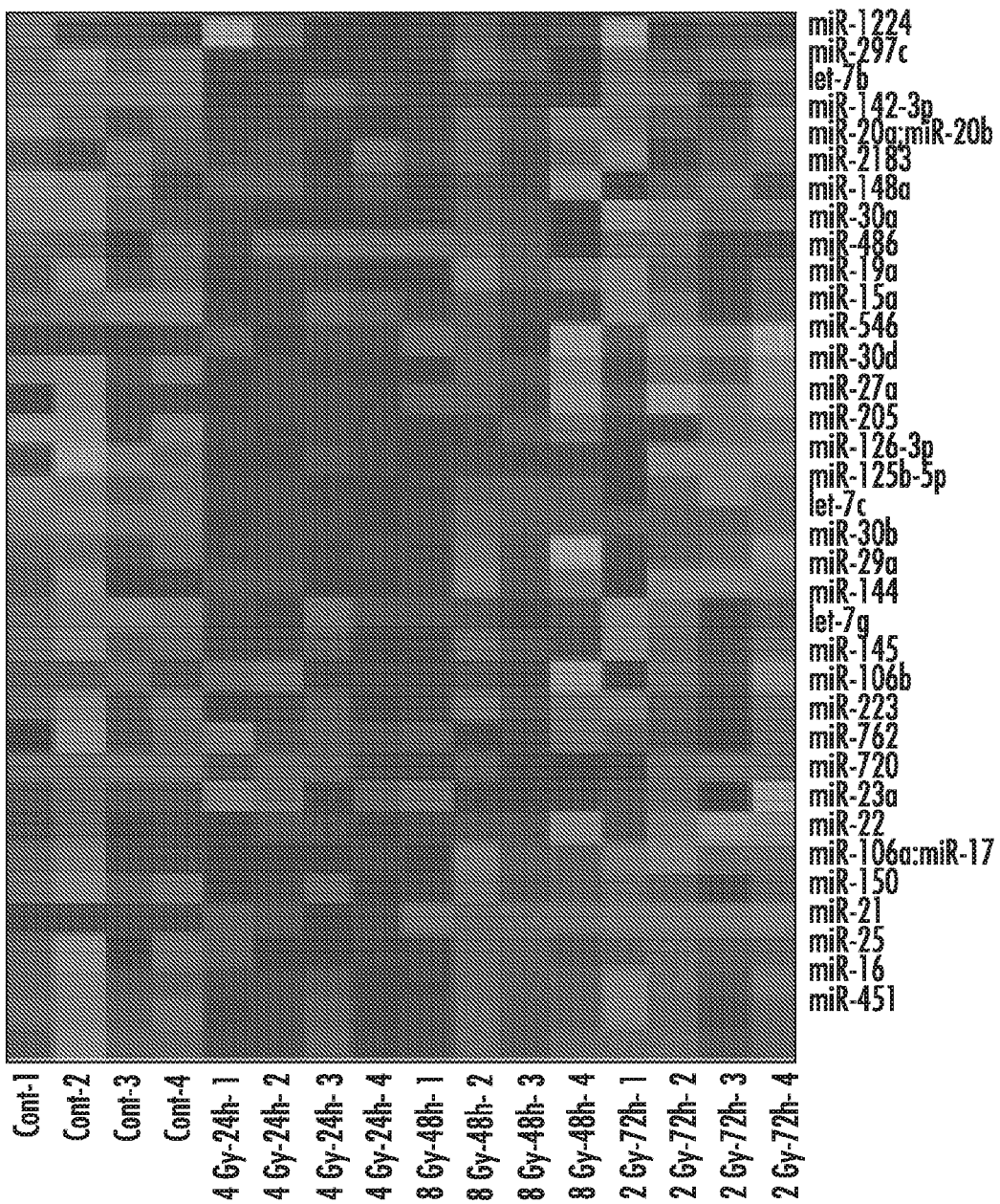
Figures 7B, 7C:
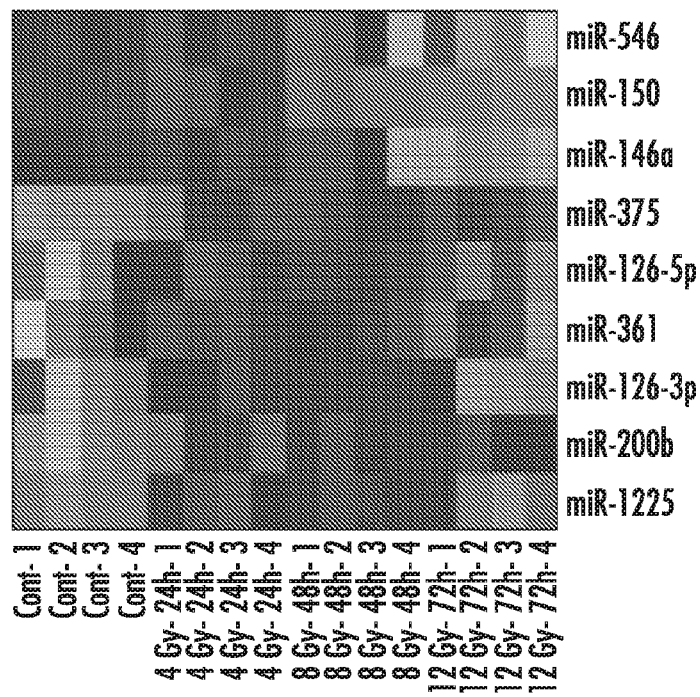
FIG. 7B is a scheme of the fractionation schedule.
FIG. 7C is a heat map for a panel of 8 miRNAs selected from ANOVA with a cutoff p-value of 0.05.
Figures 8A, 8B, 8C, 8D:
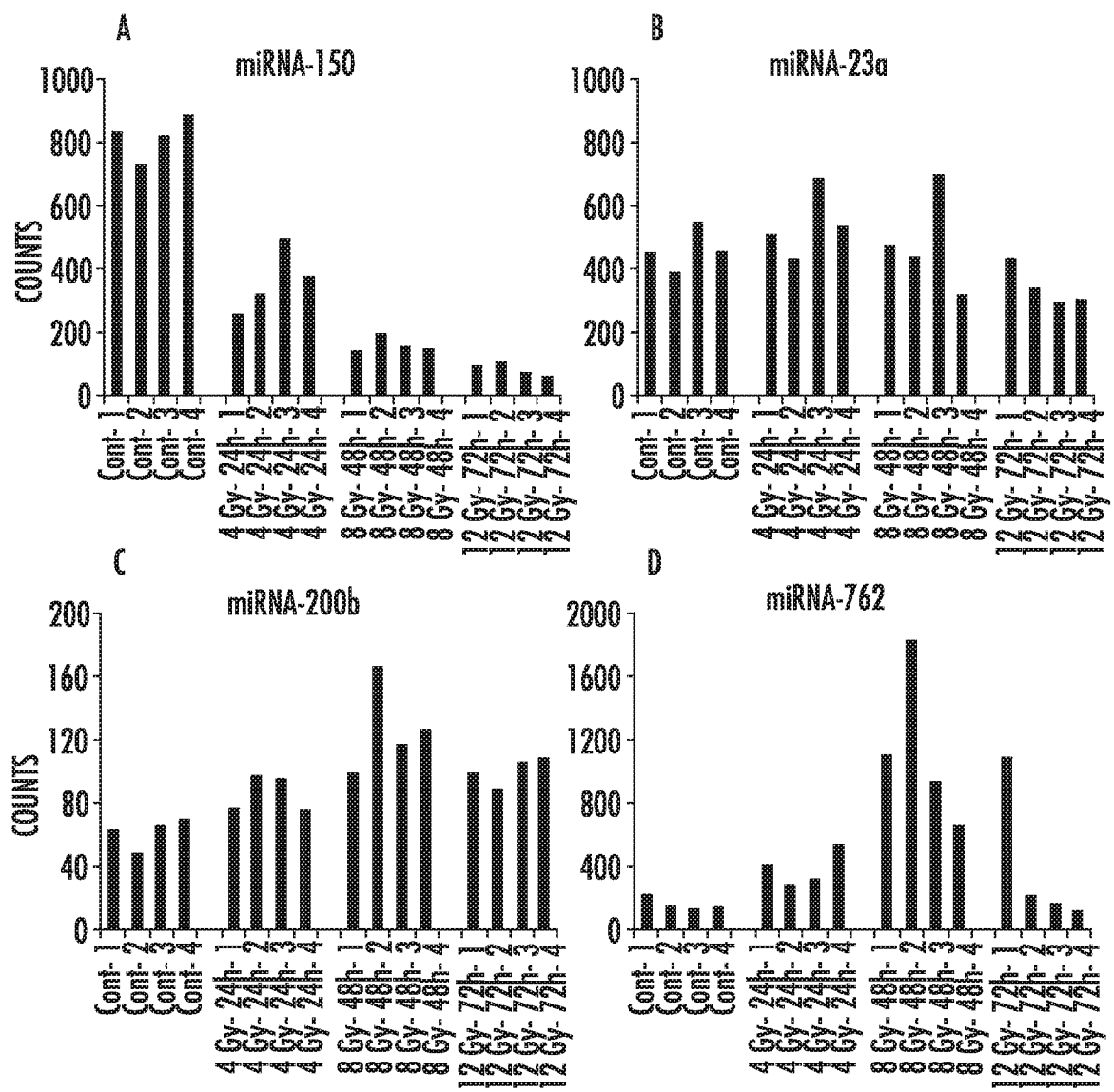
FIGS. 8A to 8D are bar graphs showing variations in the counts of miRNA-150 (FIG. 8A), miRNA-23a (FIG. 8B), miRNA-200b (FIG. 8C), and miRNA-762 (FIG. 8D) following fractionated radiation. The fluorescent counts obtained after normalization were plotted for individual animals with the dose and time as given.

In order to further investigate the biodosimetry potential of the identified miRNAs in the setting of clinical therapeutic radiation, the changes in miRNAs in animals exposed to fractionated doses was compared. Mice were exposed to fractionated radiation following a schedule comparable to that administered to patients receiving total body irradiation as preparative regimen prior to bone marrow transplantation. Twelve week old mice were exposed to a total dose of 4, 8 and 12 Gy in 2 Gy fractions twice a day. Serum collected at 24 hrs (2×2 Gy=4 Gy), 48 hrs (4×2 Gy=8 Gy) and 72 hrs (6×2 Gy=12 Gy) was analyzed for changes in miRNAs using the multiplex nCounter® platform (FIG. 7). Serum collected from the same animals three weeks prior to radiation exposure was used to compare their basal levels, and the dose and time dependent changes. Moreover, several of those miRNAs that responded to acute single dose was found sensitive to fractionated radiation as well. Consistent with data from single acute dose, about 50% reduction in serum counts for miRNA-150 was observed in mice that received 4 Gy by 24 hrs. A further decrease was observed with higher doses at later time points (FIG. 8). Consistent with the response to single acute dose, markers such as miRNA-762 and miRNA-200b exhibited an increase in their serum levels under conditions of fractionated radiation up to 48 hrs. However, a decrease in miRNA-762 was observed at 72 hours. Overall, the data establishes the biodosimetry potential of selected miRNAs under conditions receiving acute single dose as well as fractionated radiation.

Discussion

The current study has identified several evolutionarily conserved miRNAs responsive to acute radiation in a dose range relevant to accidental radiation exposure or clinical radiation therapy. Identification of serum abundant radioresponsive and non-responsive miRNAs together with spike-in oligos provide a panel of markers and controls for developing radiation biodosimeters. This will aid rapid diagnostic screening to identify individuals who are at risk of developing acute radiation syndromes. Accurate dose evaluation is critical for making medical decisions and timely administration of mitigators to prevent or reduce the acute and late effects. Individual miRNAs such as miRNA-150 alone or in combination with other markers have the potential to estimate the dose to which the individual was exposed. The majority of serum miRNA markers did not respond to radiation, but the hierarchical clustering has identified several markers, potentially originating from blood cells, exhibiting dose- and time-sensitive responses to acute single or fractionated dose. In this study, 24 and 48 hr time points were used, which are realistic time frames to collect blood samples in a scenario involving mass causality from radiation exposure. miRNA-150 depletion kinetics indicate that the response is fast and robust with a near complete depletion in 48-72 hrs with 8 Gy acute dose and 8-12 Gy fractionated dose. The evaluation of the kinetics of depletion of miRNA-150 during three days of fractionation, using a schedule followed in a clinical setting, signifies the translational potential of this marker. In addition to chemo-based approaches, fractionated total body irradiation is used for conditioning in patients undergoing bone marrow transplantation. At the same time, management of hematopoietic injury is a major clinical question in both chemo and radiation based cancer therapies.

miRNA-150 is shown herein to be a sensitive biomarker for damage to the hematopoietic system, which is the most radiosensitive organ/system. The biodosimetry potential of miRNA-150 is evident from its time and dose dependent depletion, correlating with lymphocyte depletion kinetics [Waselenko J K, et al. (2004) Ann Intern Med 140:1037-1051; Blakely W F, et al. (2010) Health Phys 99 Suppl 5: S184-191; Goans R E, et al. (1997) Health Phys 72: 513-518]. Moreover, miRNA-150 is abundant in serum (ranked among the top 6 miRNAs in serum), and was found to be sensitive even at 1 Gy, the lowest tested dose in the current study. The time and dose response of this marker makes it a potential alternative to complete blood counts and lymphocyte depletion kinetics, the current diagnostic tools for evaluating radiation response.

Example 2: Organ Specific Biological Response to Radiation

Abstract

Figure 9A:
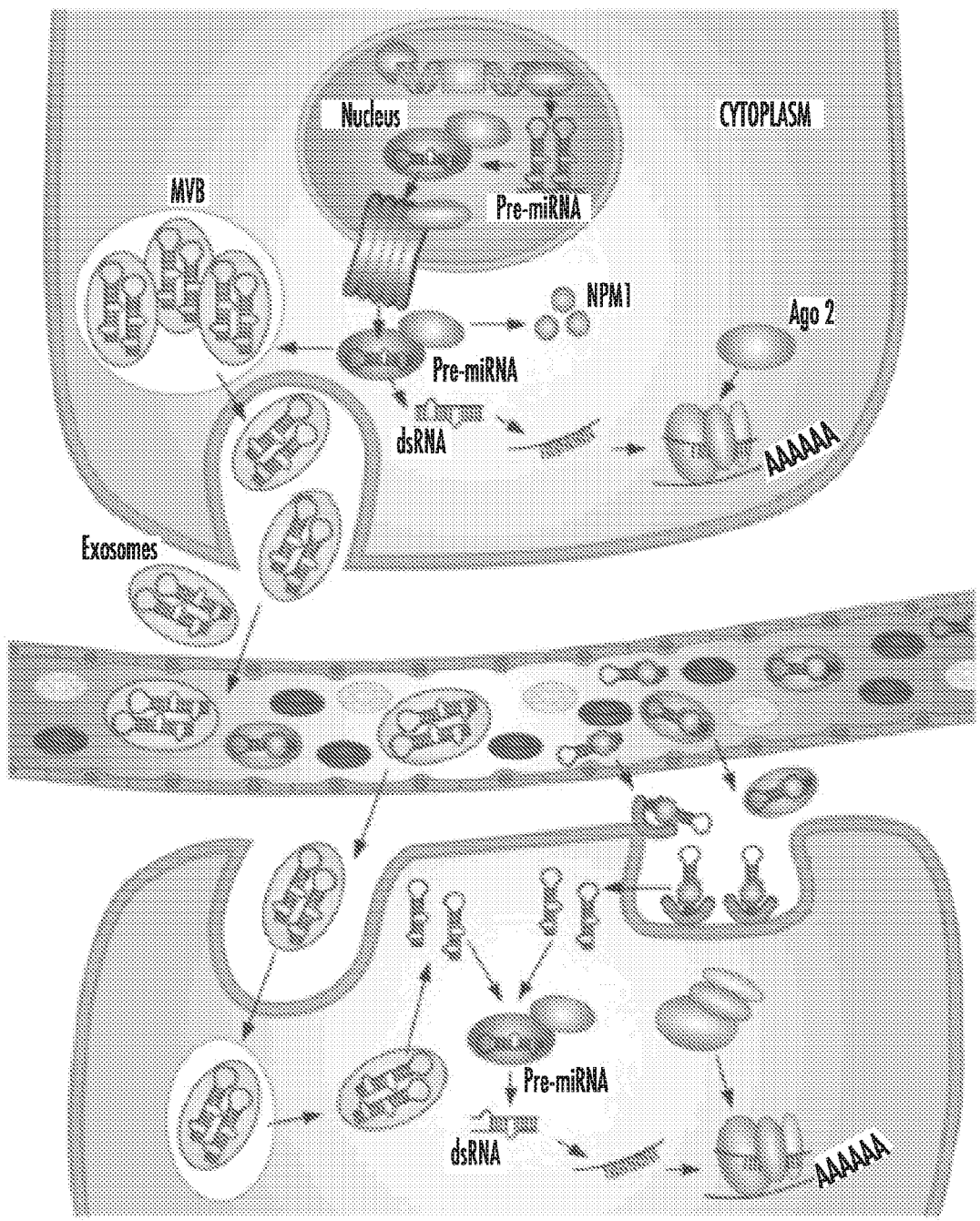
FIG. 9A illustrates the mechanism of release of miRNAs to blood stream.
Figure 9B:
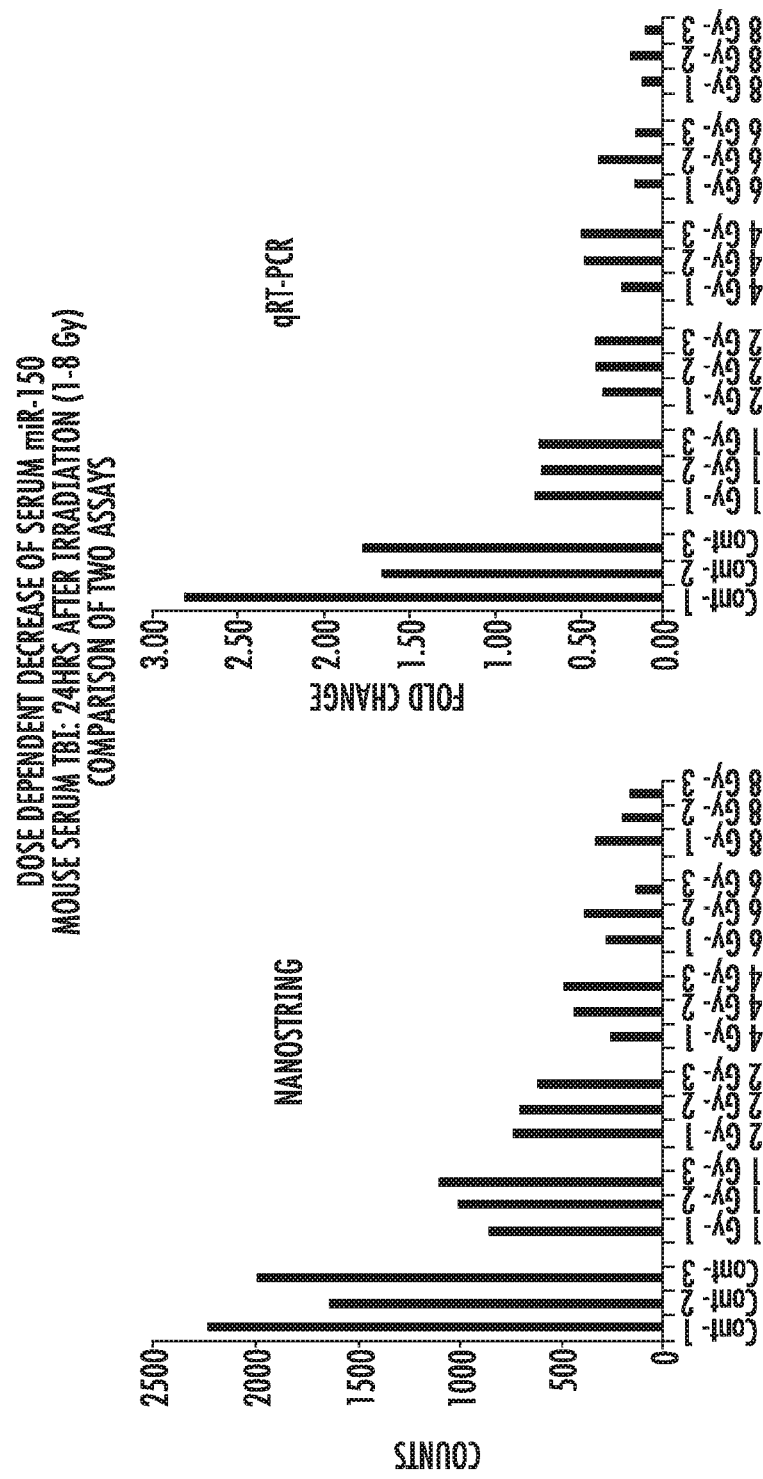
FIG. 9B shows miR-150 dose response after 48 hrs by nanoString™ and qRT-PCR, normalized with spike-in oligos.
Figure 9C:
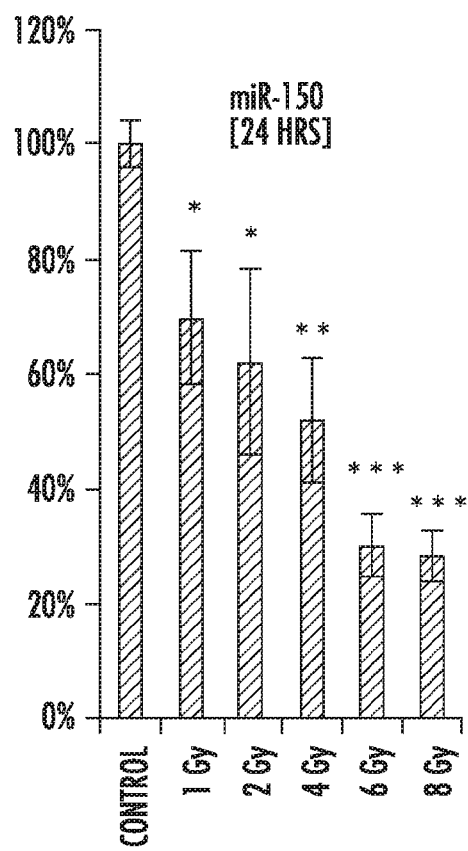
FIGS. 9C and 9D show the dose/time response of miR-150 in mouse serum (FIG. 9C) and rhesus monkey plasma (FIG. 9D). (*NHP-Rhesus macaques: Sample courtesy: ChromoLogic LLC).
Figure 9C:
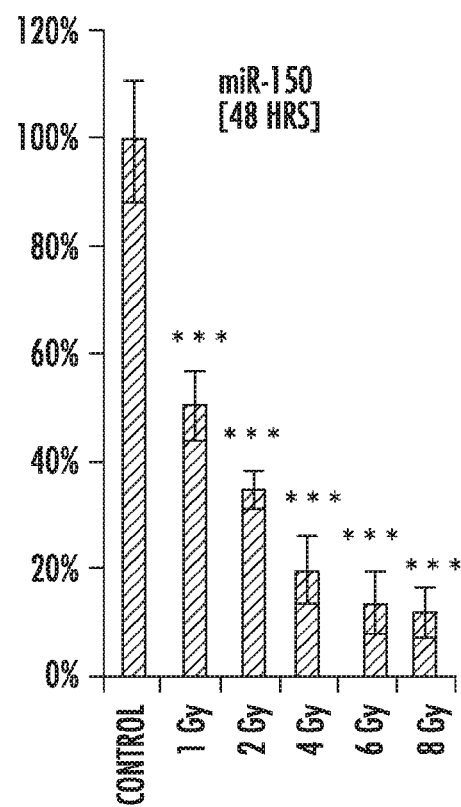
Figure 9D:
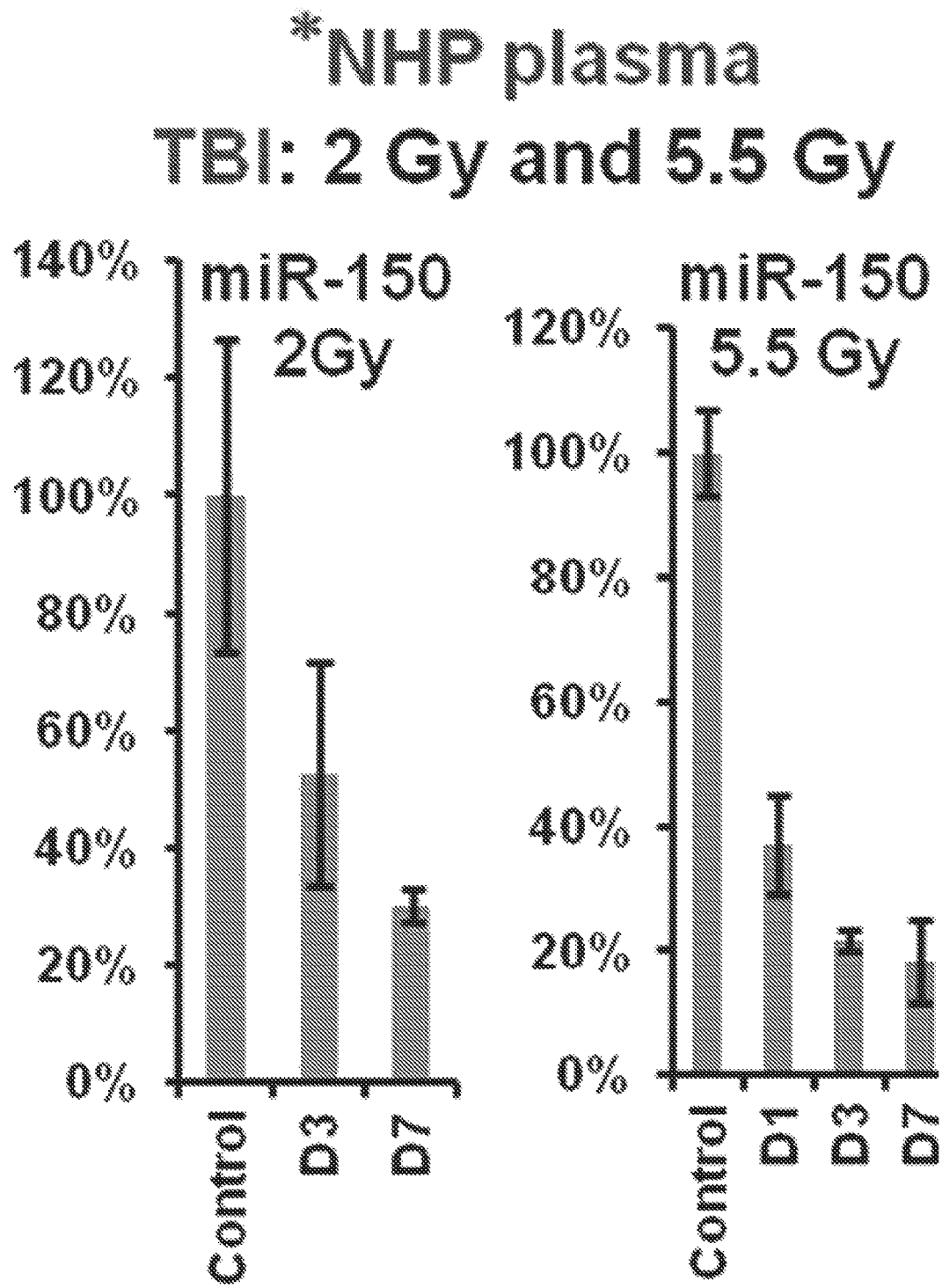
Figure 10A:
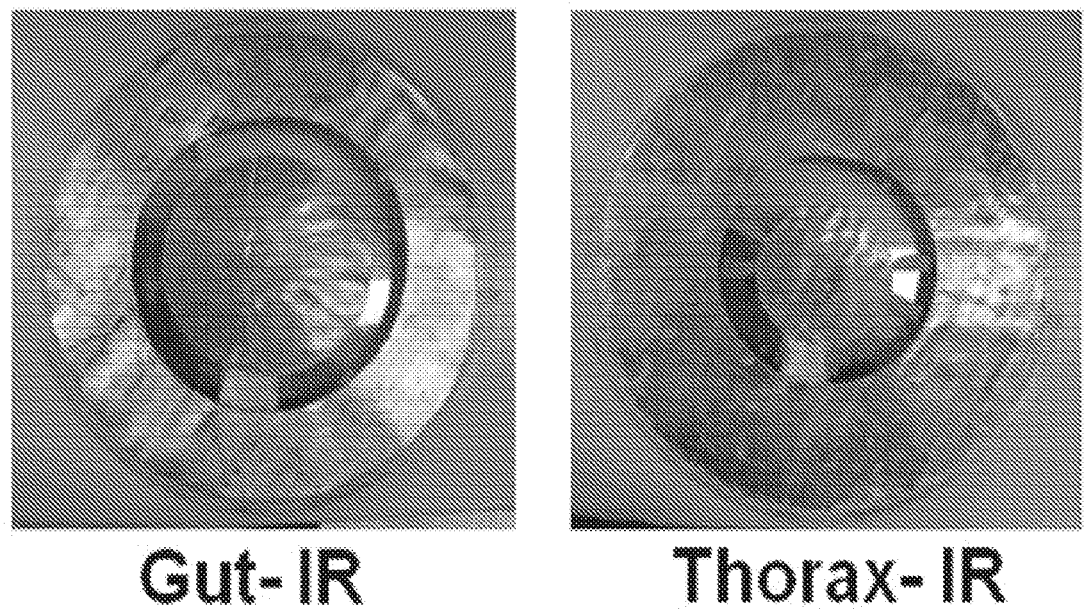
FIG. 10A shows a sample set up for gut/whole thorax exposure.
Figure 10B:
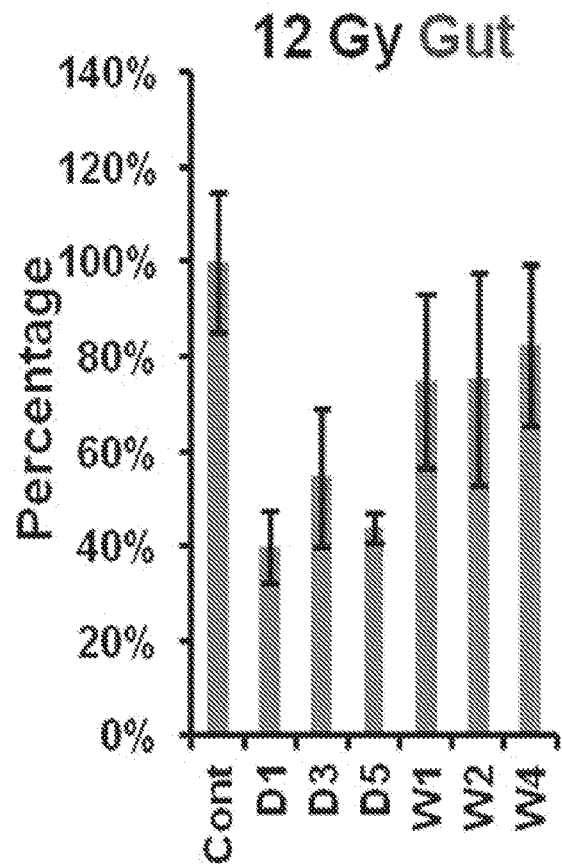
FIG. 10B shows the kinetics of miR-150 after gut irradiation (n=3)
Figures 10C, 10D:
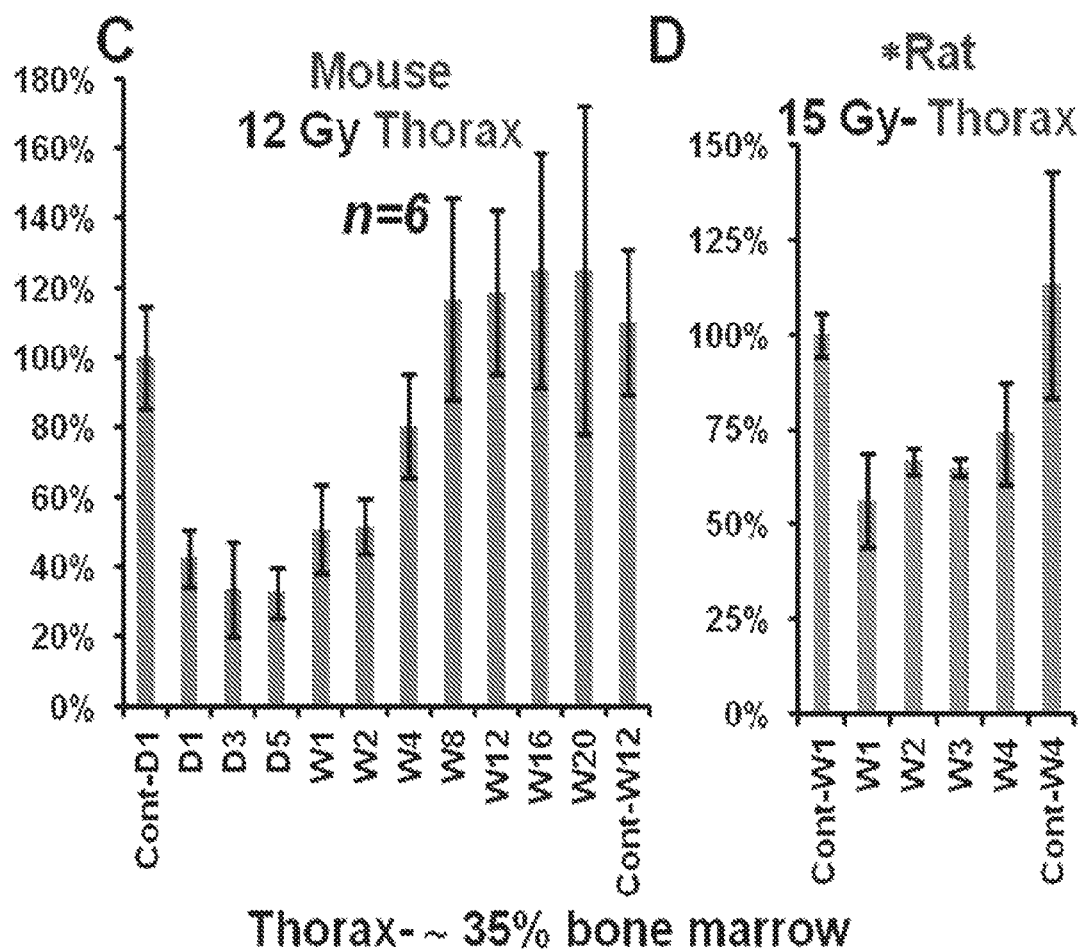
FIGS. 10C and 10D show miR-150 kinetics after whole thorax lung irradiation (WTLI) in mouse (FIG. 10C, n=6) and in rats (FIG. 10D, n=4). Two sets of animals were used to bleed at early time points.

A major issue that affects the decision making in triage after radiation accidents is the heterogeneity due to variations in exposures [Prasanna, P. G., et al. (2010) Radiat Res 173(2):245-53; Rea, M. E., et al. (2010) Health Phys 98(2): 136-44]. In a partial body exposure event, depending on dose and geography of exposure, effect may be restricted to a single or multiple organs [DiCarlo, A. L., et al. (2011) Disaster Med Public Health Prep 5 Suppl 1:S32-44]. As such, ARS follows a deterministic effect whereby dose effects have distinct clinical outcomes: generally <2 Gy exhibit mild symptoms, 2-6 Gy are primarily hematologic (HE) effects, and above 5-6 Gy gastrointestinal (GI) effects are prominent which progress more rapidly [DiCarlo, A. L., et al. (2011) Disaster Med Public Health Prep 5 Suppl 1:S32-44; Waselenko, J. K., et al. (2004) Ann Intern Med 140(12):1037-51]. Damage to the GI system should be evident within days, however require a relatively higher dose than that needed to affect the HE system. Lung is a relatively sensitive organ; but the effects will not be apparent for weeks or even months [Garofalo, M., et al. (2014) Health Phys 106(1):56-72]. The current biodosimeters (lymphocyte depletion kinetics and dicentric chromosome assays) read the response in hematopoietic system. Because of the differences in the kinetics and latency period, it is difficult to detect and/or distinguish the effects on non-HE systems. In addition, the threshold and latency period could differ due to differences in age, immune status and other underlying conditions.

miRNAs as Radiation Response Markers miRNAs are small RNA molecules of 20-24 nt long originally identified as regulators of gene expression [Bartel, D. P., et al. (2004) Cell 116(2):281-97]. They are abundant in body fluids and hence provide useful tools for diagnosis by minimally-invasive assay. In body fluids including serum and plasma, miRNAs are protected in exosomes, microparticles, and nucleoprotein complexes. Thus, they are stable at room temperature for days and even after several freeze-thaw cycles [Mitchell, P. S., et al. (2008) Proc Natl Acad Sci USA 105(30):10513-8]. Being small, they are less susceptible to degradation. Levels of specific miRNAs in blood can change after radiation by multiple ways. Like in the case of mRNAs, expression level can be altered after radiation [Templin, T., et al. (2012) Int J Radiat Biol. 87(7):653-62]. They can be released with apoptotic bodies and/or by active secretory pathways. It has been shown that processing of the precursors of miRNAs can directly or indirectly be regulated by cytokines such as Tumor Necrosis Factor-$\alpha$ (TNF$\alpha$) and TGF$\beta$1 [Barcellos-Hoff, M. H., et al. (1998) Radiat Res 150(5 Suppl):S109-20; Zhu, Y., et al. (2010) Int J Clin Exp Med 3(3):211-22; Davis, B. N., et al. (2008) Nature 454 (7200):56-61] that can be altered after radiation. Also, radiation induced activation of ATM kinase can cause alteration of the precursors in miRNAs [Zhang, X., et al., et al. (2011) Mol Cell 41(4):371-83]. Finally, reduction in a particular cell type (e.g. lymphocytes) will result in reduced circulating exosomes originated from that cell.

miR-150 as a Biodosimeter:

An amplification-free hybridization based nCounter® assay (>600 probes) was used to measure changes in over 80 miRNAs in serum after irradiation (gamma rays, 1.11 Gy/min, from Cs-137 source) [Jacob, N. K., et al. (2013) PLoS ONE 8(2):e57603]). A volume based normalization was used with a mixture of three spike-in oligos. Among various evolutionarily conserved miRNAs, miR-150 was identified as highly sensitive biomarker whose serum depletion correlates with radiation dose. miR-150 regulates B-cell development and is abundant in lymphocytes [Garzon, R., et al. (2008) Curr Opin Hematol 15(4):352-8; Adams, B. D., et al. (2012) Cell Rep 2(4):1048-60; Xiao, C., et al. (2007) Cell 131(1):146-59; Zhou, B., et al. (2007) Proc Natl Acad Sci USA 104(17):7080-5; Jiang, X., et al. (2012) Cancer Cell 22(4):524-35; Bezman, N. A., et al. (2011) J Exp Med 208(13):2717-31]. In mice that received acute single doses of 1, 2, 4, 6 and 8 Gy gamma-rays, a 30%, 38%, 48% 70% and 72% reduction of serum miR-150 was observed at 24 hrs, which was further reduced at later time points (FIG. 9B/9C). The results were confirmed by alternative methods such as qRT-PCR and RNA sequencing (FIG. 9B). Similar dose and time response were observed in plasma samples from irradiated rhesus monkeys. Time- and dose-dependent decrease in miR-150 was observed following the critical dose of 2 Gy and a higher dose of 5.5 Gy (FIG. 9D). Significant change in miR-150 levels was also noted in animals that received 0.5 Gy TBI, although response was less dramatic in the acute stage, but increased at one week post XRT. In the WTLI and gut irradiation models, a partial depletion in miR-150 was noted, however the level returned to baseline in 3 weeks, suggesting that it is an indicator of bone marrow damage and/or recovery (FIG. 10).

Identification of Biomarkers Connected with Organ-Specific Responses to XRT:

There are over 2000 miRNAs in mammalian cells and each cell type has a distinct signature with regard to their expression and abundance. For example miR-451, miR-142-3p, miR-223, etc. are high in bone marrow and blood cells, while miR-126 and let7 family, miR-29a and others are abundant in lung. HE system and lung constantly release exosomes with their respective signatures. Changes in serum miRNAs with distinct signature and kinetics were observed after WTLI. For example, increases in miR-21 and miR-29a were observed 2 weeks after WTLI, a time point where inflammation and active release of exosomes or leaking are predicted [Rube, C. E., et al. (2000) Int J Radiat Oncol Biol Phys 47(4):1033-42]. Several of the markers that peaked in the serum at 2 weeks were found to be very abundant in lung (FIG. 11, Table 1). Organ specificity was confirmed with parallel analysis failing to detect these miRs in serum samples collected from control animals or animals exposed to GI radiation (FIG. 11). Further, several of these miRs are reported to be altered in lung diseases, or are mechanistically connected to responses such as lung injury and/or inflammation [Hassan, F., et al. (2012) PLoS ONE 7(11):e50837; Izzotti, A., et al. (2009) Faseb J 23(3):806-12; Oglesby, I. K., et al. (2010) J Immunol 184(4):1702-9]. Delayed effects of radiation, such as pneumonitis, were evident from microCT and MRI analysis at around 20 weeks after radiation in several animals (data not shown). Dose effects were evident from the differences in serum markers, latency and incidence of delayed effects, when compared 8 Gy vs 12 Gy exposed animals. Overall, data from organ targeted/protected irradiation animals led to the development of a panel of miRNA biomarkers that provide references for evaluating organ responses after partial body exposure.

TABLE 1 miRNA markers with distinct response with potential connection with organ function, along with several controls.

| Organ | Response/Connection | Serum/Plasma miRs identified |
|---|---|---|
| Lung | | |
| 1-3 days | Tissue/DNA damage/ Apoptosis/systemic response | miR-200b, miR-191-5p, miR-144-3p, miR-146a, miR-142-3p, miR-192 |
| 2 weeks | Inflammatory response/ Lung injury/leakage | miR-21, miR-29a, miR-126-3p, let-7c, miR-191-5p, miR-15b, miR-130a, miR-19a |
| 8+ weeks | Pneumonitis/progression/ systemic effects | miR-146a, miR-486, miR-25, miR-192 |
| HE | HE stem cells depletion/ recovery | miR-150 |
| GI | TLR signaling | miR-574-5p (6-10 fold increase in NHPs, 5.5 Gy 24 h) |
| Controls | Hemolysis | miR-451, miR-16, miR-106b |
| | Internal Controls | miR-30a, miR-23a, miR130b |
| | Cellular RNA contamination | Actin, Tubulin, Gapdh, Rp119 |
| | Normalizers (spike-ins) | At-159a, Cel-248, Osa-414 |

Example 3: Diagnosis of Radiation Induced Lung Injury, Pneumonitis, and Lung Fibrosis BALB/c mice received 12 Gy whole thorax lung irradiation (WTLI), resulting in pneumonitis and death at 20-22 weeks. Rhesus monkeys received 9 Gy or 11.5 Gy WTLI (9 Gy is a sublethal dose, while 11.5 Gy is lethal). All the 11.5 Gy animals had to be euthanized by day 100, while 9 Gy animals were found normal. So, the markers identified here will distinguish the lethal versus sub-lethal dose in the first week itself. Serum/Plasma was collected at C-D1, D1, D3, D5, Wk1, Wk2, Wk4, Wk8, Wk12, and C-12Wk for mice; and D0, D1/2, D5, and D8 for monkeys.

Figure 12:
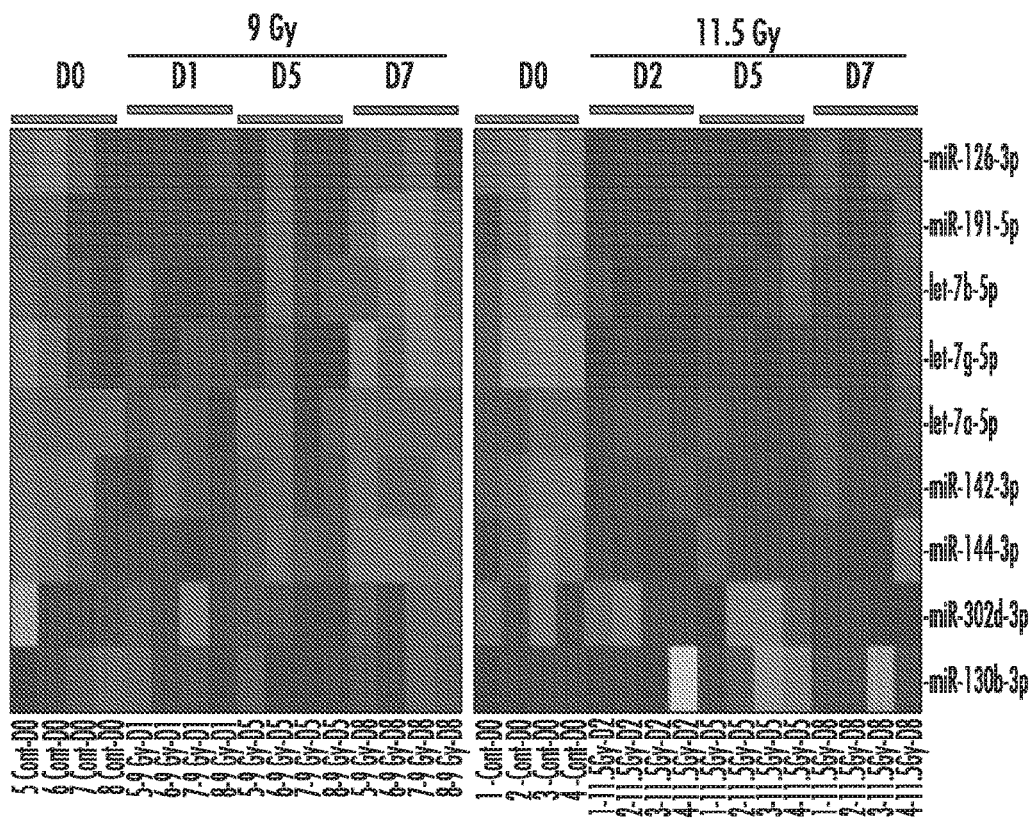
FIG. 12 is a heatmap showing results of 6 marker panel (and 2 controls) for plasma collected from rhesus monkeys that received 9 Gy or 11.5 Gy whole thorax irradiation (WTI).

FIG. 12 is a heatmap showing results of 6 marker panel (and 2 controls) for the rhesus monkey-WTLI model.

Figure 13A:
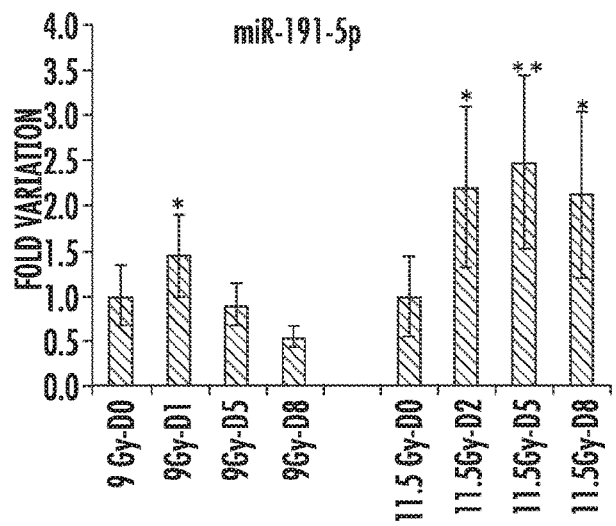
FIGS. 13A to 13C are bar graphs showing miR-191-5p (FIG. 13A), miR-144-3p (FIG. 13B), and miR-302-3p (FIG. 13C) expression as a function of WTI dose and time.
Figure 13B:
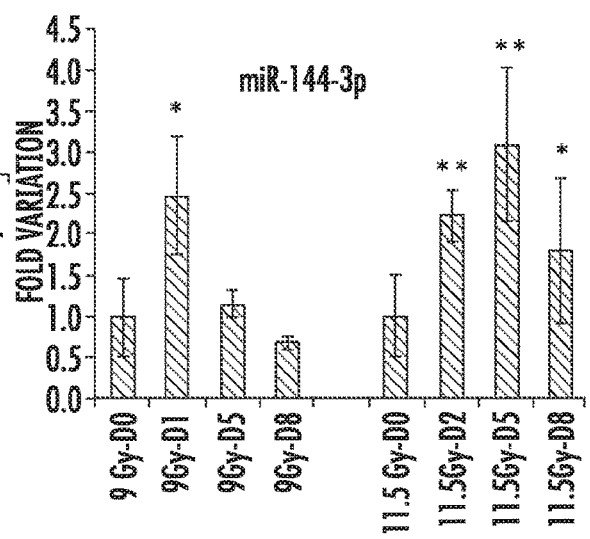
Figure 13C:
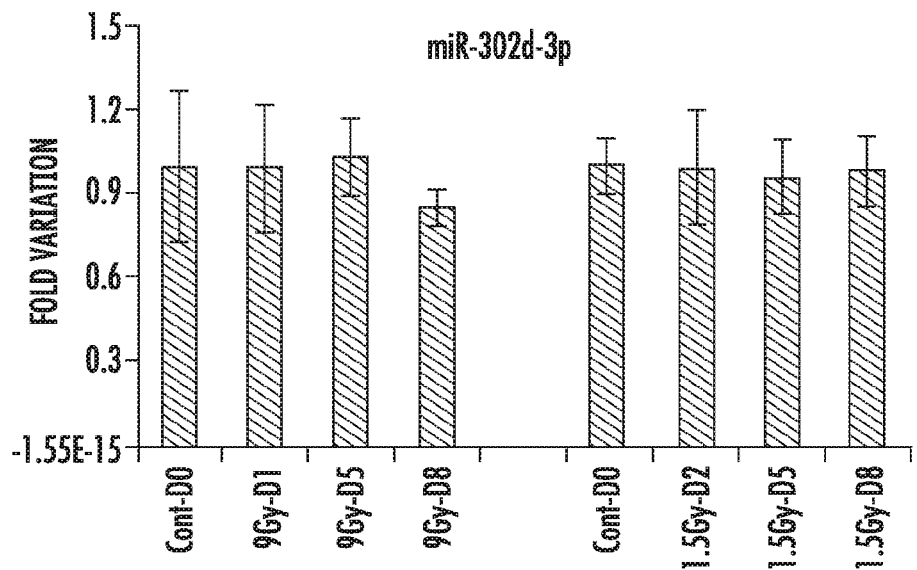

FIGS. 13A to 13C are bar graphs showing miR-191-5p (FIG. 13A), miR-144-3p (FIG. 13B), and miR-302-3p (FIG. 13C) expression as a function of WTLI dose and time. miR-191-5p is upregulated in lung exposed to cigarette smoke (targets Nrf2). miR-144-3p is altered in idiopathic pulmonary fibrosis (IPF), cystic fibrosis (CF), etc., and targets CFTR gene. miR-302-3p was used as an internal control.

Figure 14A:
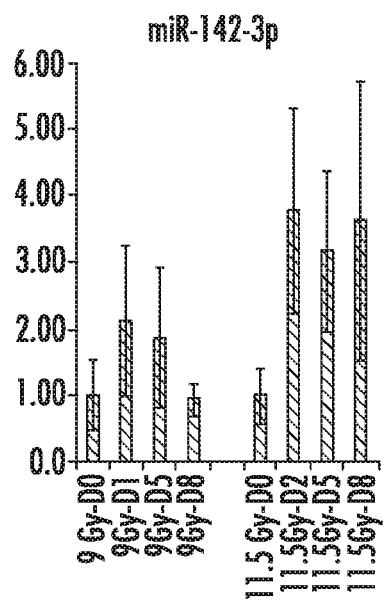
FIGS. 14A to 14C are bar graphs showing miR-142-3p (FIG. 14A), miR-126-3p (FIG. 14B), and let-7g-5p (FIG. 14C) expression as a function of WTI dose and time.
Figure 14B:
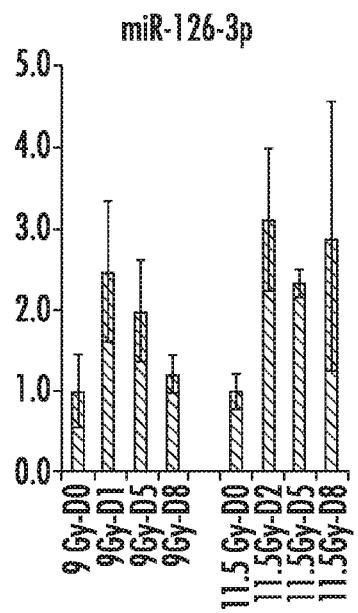
Figure 14C:
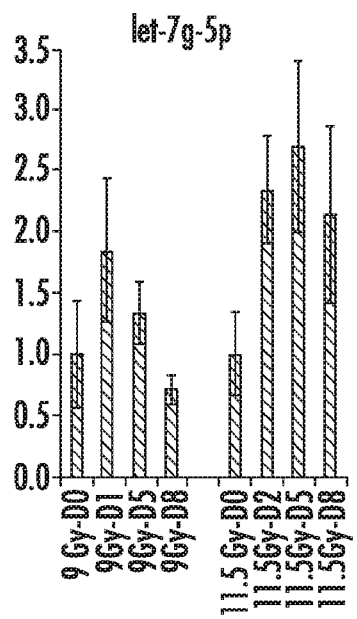

FIGS. 14A to 14C are bar graphs showing miR-142-3p (FIG. 14A), miR-126-3p (FIG. 14B), and let-7g-5p (FIG. 14C) expression as a function of WTLI dose and time. miR-142-3p regulate innate immune response functional regulation of IL-6 in dendritic cells. miR-126-3p expression is down in CF airway epithelial cells, and regulates innate immune response. let7 family abundant in lung and implicated in lung diseases.

Figure 15A:
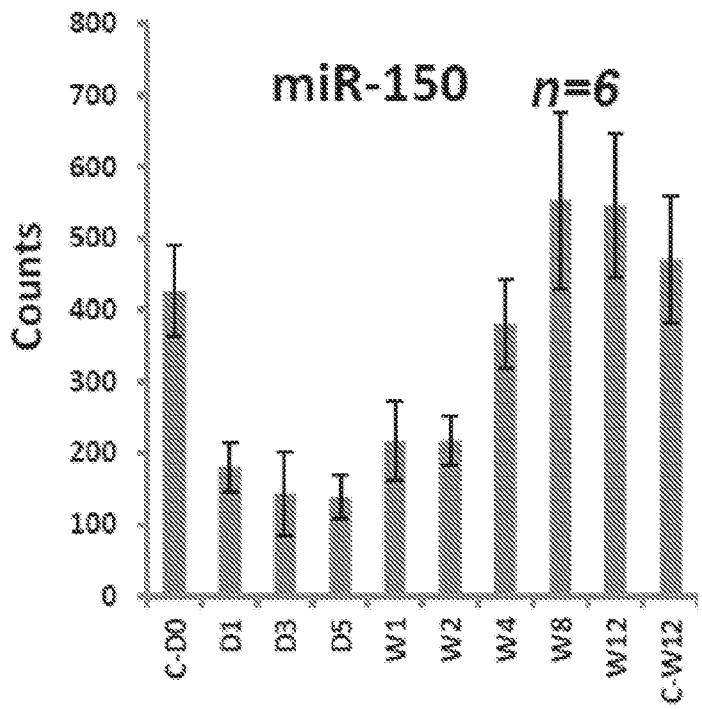
FIGS. 15A to 15N are bar graphs showing serum (FIGS. 15A, 15C, 15E, 15G, 15I, 15K, 15M) and lung (FIGS. 15B, 15D, 15F, 15H, 15J, 15L, 15N) levels of miR-150 (FIGS. 15A, 15B), miR-21 (FIGS. 15C, 15D), miR-200b (FIGS. 15E, 15F), miR-29a (FIGS. 15G, 15H), miR-146a (FIGS. 15I, 15J), miR-126-3p (FIGS. 15K, 15L), and miR-192 (FIGS. 15M, 15N) after WTI.
Figure 15B:
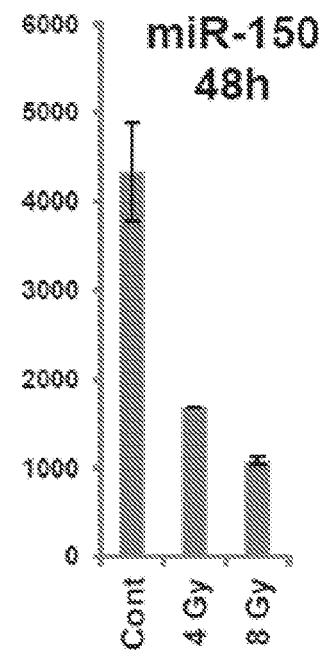
FIG. 15O shows serum levels of miR-192 after gut irradiation.
Figure 15C:
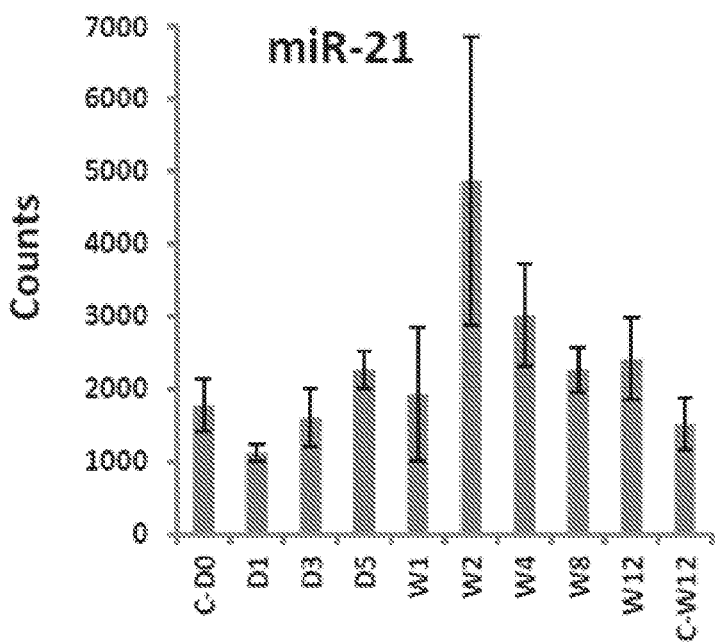
Figure 15D:
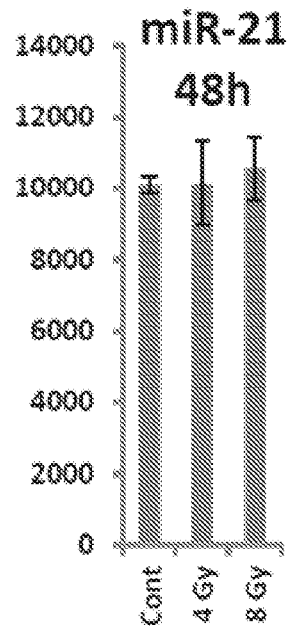
Figure 15E:
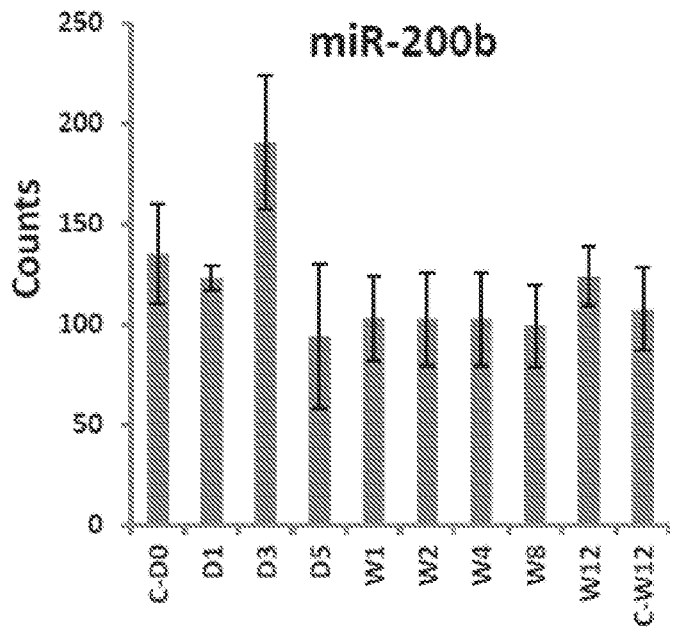
Figure 15F:
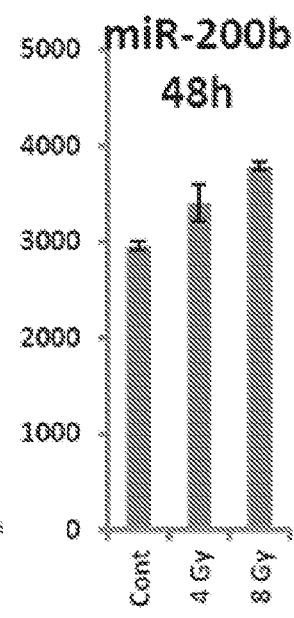
Figure 15G:
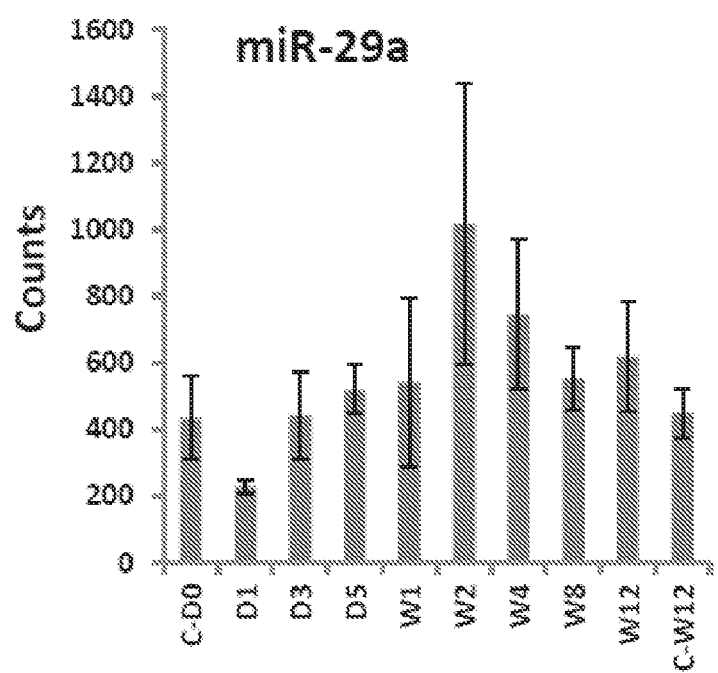
Figure 15H:
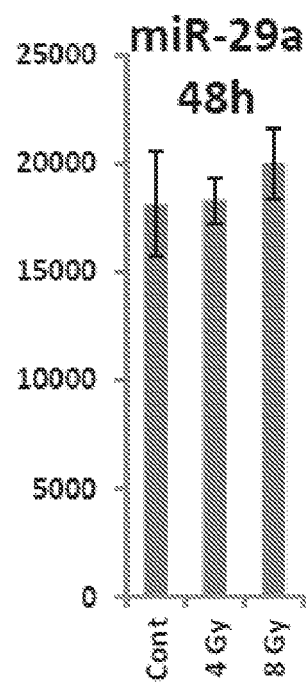
Figure 15M:
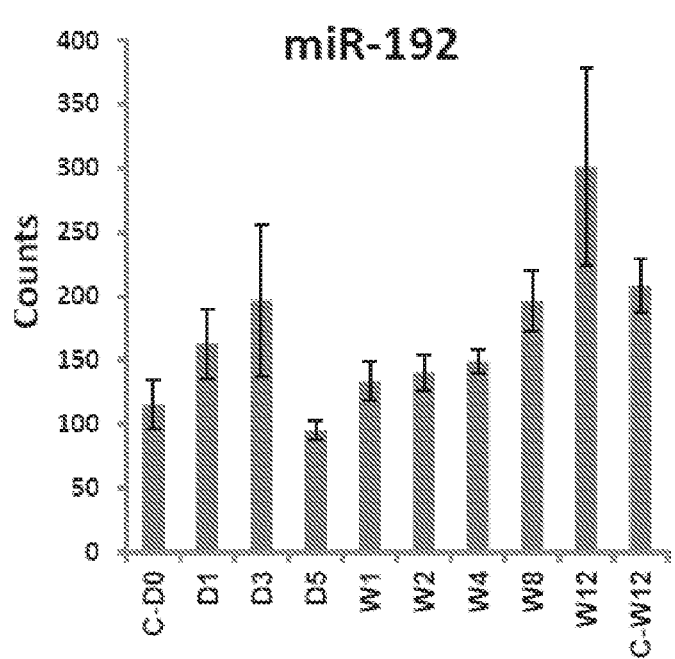
Figure 15N:
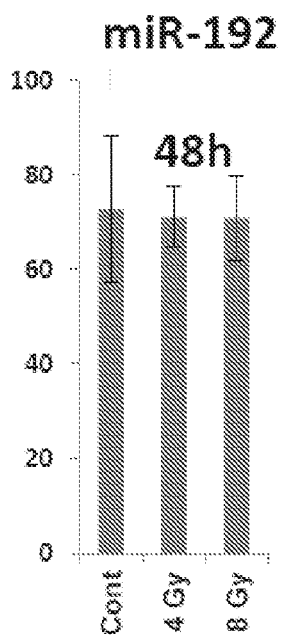
Figure 15O:
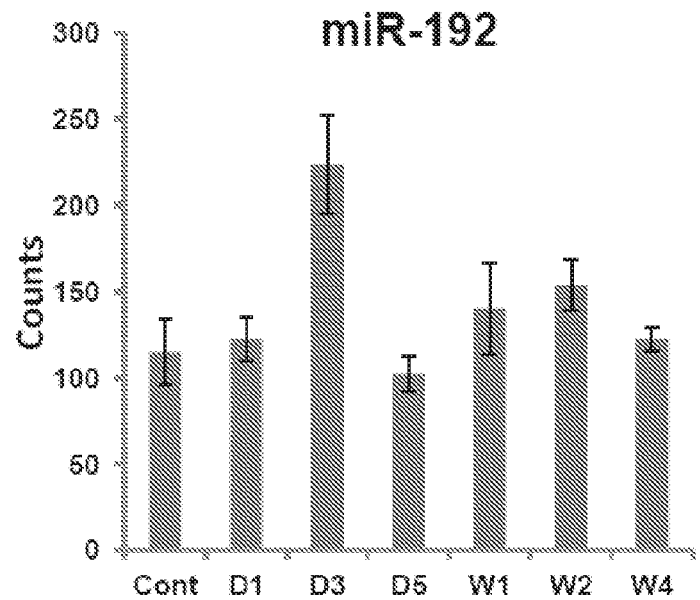
Figure 16A:
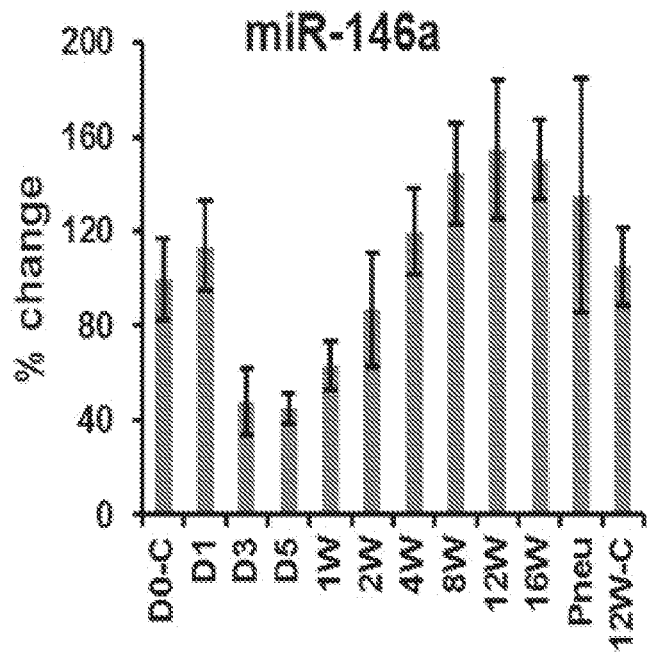
FIGS. 16A to 16C show selected early, late markers detected in BALB/c WTLI (12 Gy) model. miR-200b (FIG. 16C) is an early systemic responder, miR-146a (FIG. 16A) is an inflammatory response marker with delayed kinetics, high miR-122 (FIG. 16B) is detected after acute pneumonitis and multi-organ failure, including live damage. Representative images of lung (FIG. 16D), MRI (FIG. 16E) and pCT (FIG. 16F) are shown.
Figure 16B:
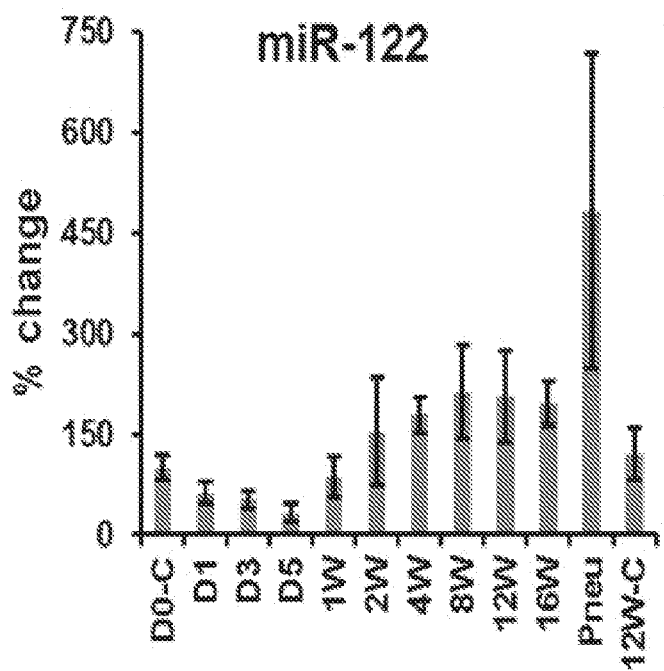
Figure 16C:
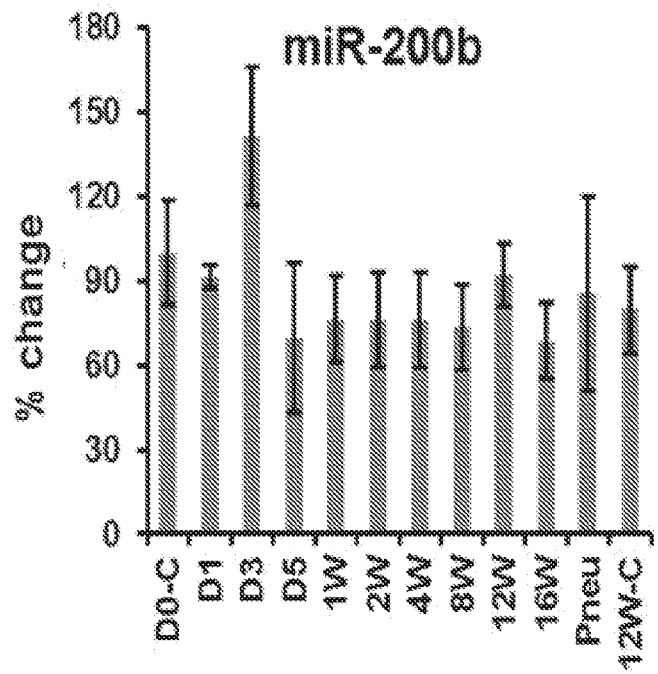
Figure 16D:
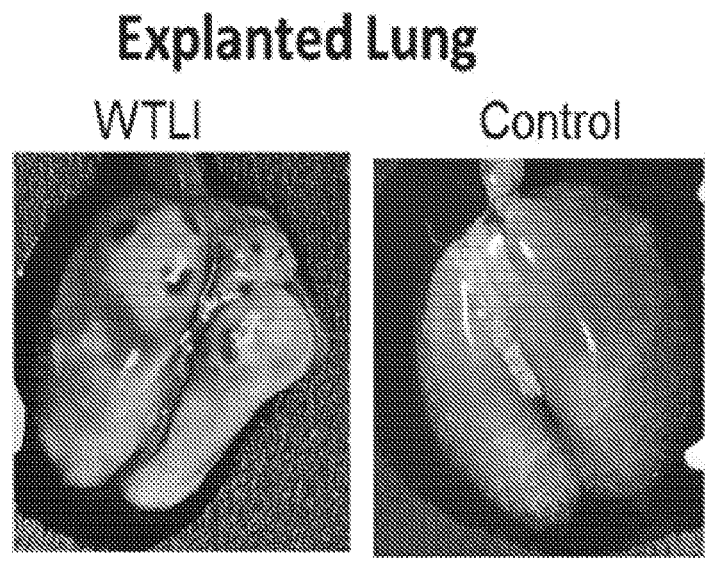
Figure 16E:
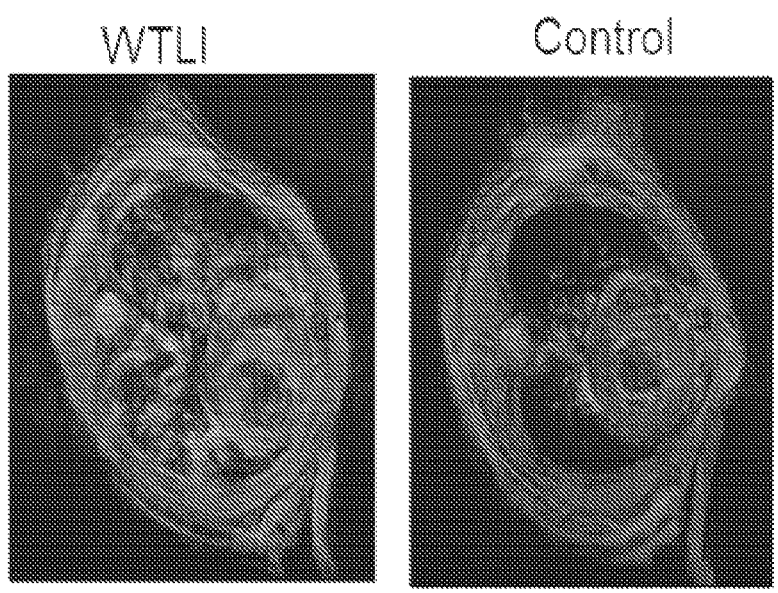
Figure 16F:
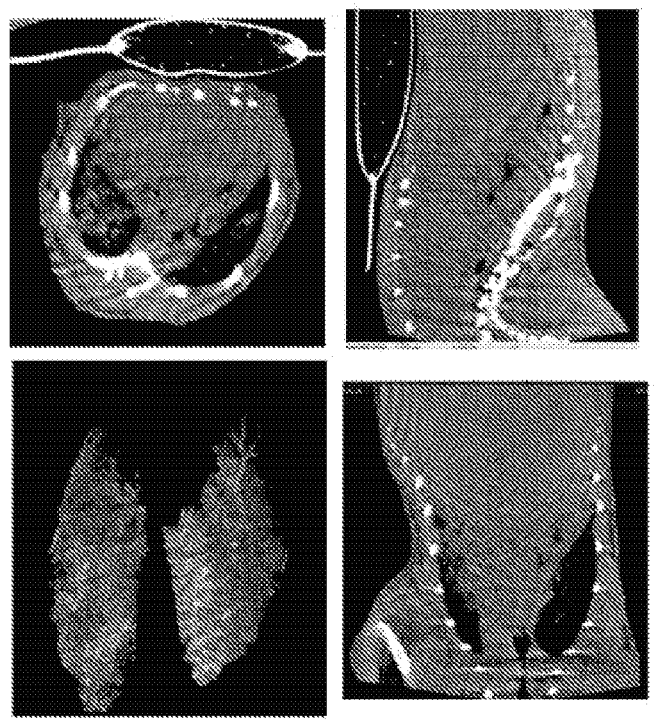
Figure 16F:
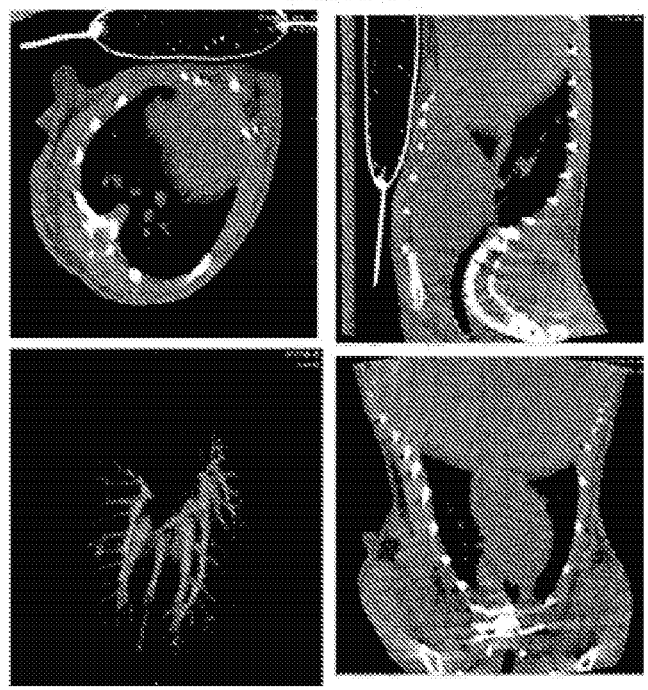
Figure 17A:
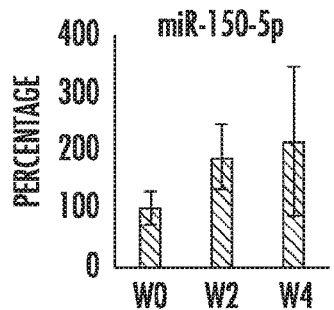
FIGS. 17A to 17I show changes in serum miR-150-5p (FIG. 17A), miR-21-5p (FIG. 17B), miR-29a-3p (FIG. 17C), miR-302d-3p (FIG. 17D), miR155-5p (FIG. 17E), miR-223-3p (FIG. 17F), miR-4454 (FIG. 17G), miR-630 (FIG. 17H), miR-22-3p (FIG. 17I) in human patients received myeloablative TBI.
Figure 17B:
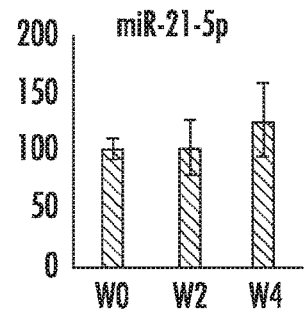
Figure 17C:
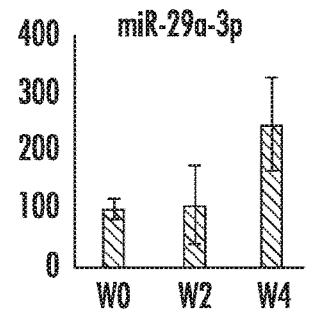
Figure 17D:
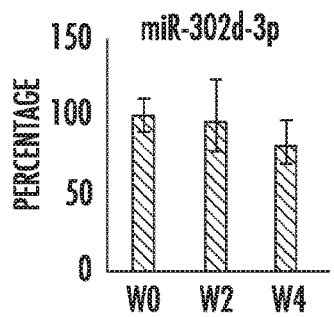
Figure 17E:
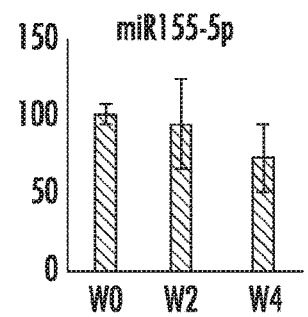
Figure 17F:
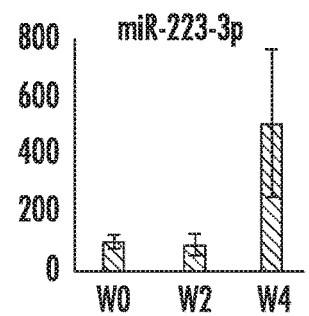
Figure 17G:
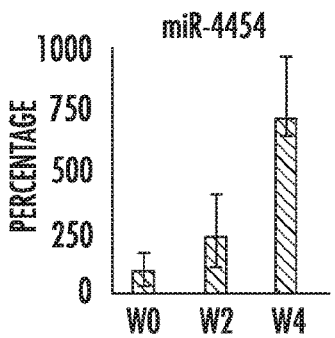
Figure 17H:
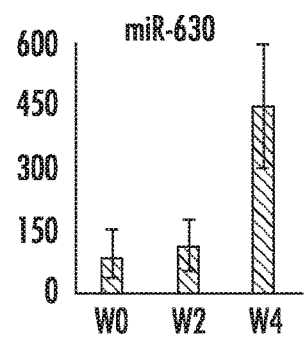
Figure 17I:
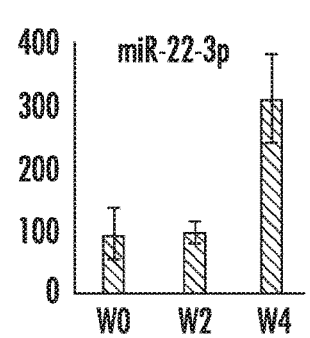

FIGS. 15A to 15X are bar graphs showing serum (FIGS. 15A, 15C, 15E, 15G, 15I, 15K, 15M) and lung (FIGS. 15B, 15D, 15F, 15H, 15J, 15L, 15N) levels of miR-150 (FIGS. 15A, 15B), miR-21 (FIGS. 15C, 15D), miR-200b (FIGS. 15E, 15F), miR-29a (FIGS. 15G, 15H), miR-146a (FIGS. 15I, 15J), miR-126-3p (FIGS. 15K, 15L), and miR-192 (FIGS. 15M, 15N) after WTI. FIG. 15O shows serum levels of miR-192 after gut irradiation.

Delayed effects of radiation, such as pneumonitis, were evident from microCT and MRI analysis in several animals (FIG. 16). Dose effects were evident from the differences in latency and incidence in 8 Gy and 12 Gy exposed BALB/c mice. Interestingly, progressive changes were observed in markers such as miR-146a that is reported to be mechanistically associated with inflammatory responses. Thus, systematically following the kinetics of circulating miRNAs in organ targeted/protected irradiation models resulted in development of a panel of biomarkers that provides minimally invasive and early readout of organ-specific responses even after partial body exposure involving multiple organs.

Radiation-induced delayed/late effects on lung after 16 Gy WTLI was also studied in C57BL6 mice. Broncho alveolar lavage (BAL) was compared at 45 and 60 days post-irradiation for the infiltration of macrophages and other inflammatory cells in lung. Thoracic radiation increased inflammatory cells in lung, a hallmark of delayed effects of radiation manifested as pneumonitis and fibrosis.

Changes in serum samples from human patients who received radiation based myeloablation prior to stem cell transplant at The OSU James Cancer Hospital was evaluated. Analysis of serum samples from 5 Leukemia patients received TBI (2 Gy×6), collected at week 0, week 2 and week 4 showed promising results (FIG. 17). Consistent with the data from animal models, conserved miRNAs were found to be altered as a function of time. Inclusion of the samples with near complete myeloablation further allowed to distinguish biomarkers of HE and non-HE origin detectable in cell-free serum. Kinetics of miR-150 shows the correlation with reconstitution kinetics, signifying the observation made in animal models, warranting analysis in larger cohorts and additional time points.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for monitoring hematopoietic reconstitution or suppression in a subject receiving ionizing radiation, comprising quantifying the levels of circulating miR-150 in a blood sample from the subject, wherein the levels of circulating miR-150 in the sample is a measure of hematopoietic reconstitution or suppression.

2. The method of claim 1, wherein the subject is the recipient of a population of hematopoietic stem cells.

3. A method for reconstituting the hematopoietic compartment of a subject in need thereof, the method comprising:
   administering to the subject a therapeutically effective amount of a population of hematopoietic stem cells to reconstitute the hematopoietic compartment of the subject; and
   monitoring efficacy of the hematopoietic reconstitution by quantifying the levels of circulating miR-150 in a blood sample from the subject, wherein the levels of circulating miR-150 in the sample is an indication of hematopoietic reconstitution.

4. The method of claim 1, wherein the subject has or had a hematological malignancy, a myeloma, multiple myeloma, a leukemia, acute lymphoblastic leukemia, chronic lymphocytic leukemia, a lymphoma, indolent lymphoma, non-Hodgkin lymphoma, diffuse B cell lymphoma, follicular lymphoma, mantle cell lymphoma, T cell lymphoma, Hodgkin lymphoma, a neuroblastoma, a retinoblastoma, Shwachman Diamond syndrome, a brain tumor, Ewing's Sarcoma, a Desmoplastic small round cell tumor, a relapsed germ cell tumor, a hematological disorder, a hemoglobinopathy, an autoimmune disorder, juvenile idiopathic arthritis, systemic lupus erythematosus, severe combined immunodeficiency, congenital neutropenia with defective stem cells, severe aplastic anemia, a sickle-cell disease, a myelodysplasia syndrome, chronic granulomatous disease, a metabolic disorder, Hurler syndrome, Gaucher disease, osteopetrosis, malignant infantile osteopetrosis, heart disease, HIV, or AIDS.

5. The method of claim 1, wherein the subject has had an organ transplant.

6. The method of claim 2, wherein the population of hematopoietic stem cells were obtained from bone marrow, from peripheral blood cells, from peripheral blood cells that have undergone apheresis, from peripheral blood cells that have undergone leukapheresis, from umbilical cord blood, from amniotic fluid, from cultured HSC cells, from an immortalized HSC cell line, or from a conditionally immortalized HSC cell line.

7. The method of claim 3, wherein the population of hematopoietic stem cells is administered as a step in a hematopoietic stem cell (HSC) transplantation procedure.

8. The method of claim 7, wherein the HSC transplantation procedure is a myeloablative HSC transplantation procedure.

9. The method of claim 7, wherein the HSC transplantation procedure is a non-myeloablative HSC transplantation procedure.

10. The method of claim 7, wherein the HSC transplantation is an autologous HSC transplantation or an allogenic HSC transplantation.

11. The method of claim 7, further comprising transplanting the HSCs when circulating miR-150 levels are undetectable.

12. The method of claim 1, wherein the method evaluates the effect of an agent that promotes hematopoietic reconstitution.

13. The method of claim 12, wherein the agent comprises GM-CSF, G-CSF, or a combination thereof.

14. The method of claim 1, wherein the method evaluates the effect of a cytotoxic drug on hematopoietic suppression.

15. The method of claim 14, wherein the cytotoxic drug comprises cysplatin, doxorubicin or 5-FU.

16. The method of claim 1, further comprising determining a hematopoietic suppression kinetic value and using that value to adjust the ionizing radiation dose.

17. The method of claim 1, wherein the subject is receiving a dose of ionizing radiation for myeoloablation.

18. A method for monitoring the effect of ionizing radiation on the lung in a subject, comprising quantifying the levels of one or more circulating microRNA in a blood sample from the subject, wherein the microRNA are selected from the group consisting of let-7c, miR-15b, miR-21, miR-25, miR-29a, miR-126-3p, miR-142-3p, miR-144-3p, miR-146a, miR-191-5p, miR-192, miR-200b, and miR-486, and wherein elevated levels of the one or more circulating microRNA in the sample is an indication of radiation-induced lung injury.

19. The method of claim 18, wherein elevated levels of miR-200b, miR-191-5p, miR-144-3p, miR-146a, miR-142-3p, miR-192, or a combination thereof, occurring in the first week after exposure is an indication of lung tissue damage.

20. The method of claim 18, wherein elevated levels of miR-21, miR-29a, miR-126-3p, let-7c, miR-191-5p, miR-15b, or a combination thereof, occurring about two to four weeks after exposure is an indication of lung inflammatory response and injury.

21. The method of claim 18, wherein elevated levels of miR-146a, miR-486, miR-25, miR-192, or a combination thereof, occurring about eight weeks after exposure is an indication of pneumonitis.

22. The method of claim 18, further comprising treating the subject for lung injury if elevated levels of the one or more circulating microRNA are detected.

23. The method of claim 22, comprising treating the subject with a corticosteroid if elevated levels of the one or more circulating microRNA are detected.

24. The method of claim 22, comprising treating the subject with an angiotensin converting enzyme inhibitors (ACEI), a hydroxymethylglutaryl coenzyme A (HMG-CoA) reductase inhibitor, or a combination thereof if elevated levels of the one or more circulating microRNA are detected.

25. The method of claim 18, further comprising treating the subject with cyclophosphamide, N-acetylcysteine (NAC), supplemental oxygen therapy, or a combination thereof if elevated levels of the one or more circulating microRNA are detected.

26. The method of claim 18, further comprising reducing the radiation dose if elevated levels of the one or more circulating microRNA are detected.

27. The method of claim 18, further comprising evaluating the efficacy of a lung treatment following radiation exposure by monitoring levels of the one or more circulating microRNA in a blood sample from the subject taken at intervals following the treatment.

* * * * *

UNITED STATES PATENT AND TRADEMARK OFFICE
CERTIFICATE OF CORRECTION

PATENT NO. : 10,513,736 B2
APPLICATION NO. : 16/195411
DATED : December 24, 2019
INVENTOR(S) : Naduparambil Jacob and Arnab Chakravarti It is certified that error appears in the above-identified patent and that said Letters Patent is hereby corrected as shown below:

In the Specification

Column 1, Line 11 add Government Support Clause "This invention was made with government support under grant number AI067798 awarded by the National Institutes of Health. The government has certain rights in the invention."

Signed and Sealed this
Sixth Day of October, 2020

Andrei Iancu
*Director of the United States Patent and Trademark Office*